US009492806B2

(12) United States Patent
Ackermann et al.

(10) Patent No.: US 9,492,806 B2
(45) Date of Patent: Nov. 15, 2016

(54) CAVITATION GENERATION MECHANISMS AND THEIR USE IN FERMENTATION AND WASTEWATER AND SAND CLEANING PROCESSES

(71) Applicants: Heiko Ackermann, Rietheim-Weilheim (DE); Emil Hepting, Bad Dürrheim (DE)

(72) Inventors: Heiko Ackermann, Rietheim-Weilheim (DE); Emil Hepting, Bad Dürrheim (DE)

( * ) Notice: Subject to any disclaimer, the term of this patent is extended or adjusted under 35 U.S.C. 154(b) by 0 days.

(21) Appl. No.: 14/102,279

(22) Filed: Dec. 10, 2013

(65) Prior Publication Data
US 2015/0336067 A1 Nov. 26, 2015

(51) Int. Cl.
*B01J 19/00* (2006.01)
*B01D 3/00* (2006.01)
(Continued)

(52) U.S. Cl.
CPC .............. *B01J 19/008* (2013.01); *B01D 3/00* (2013.01); *B01D 3/006* (2013.01); *B01D 3/10* (2013.01);
(Continued)

(58) Field of Classification Search
CPC .......... B01J 19/008; B08B 3/12; B01D 21/28; B01D 3/00; B01D 3/10; B01D 3/006; C07C 63/07; C07C 67/02; B01F 11/0077; B01F 13/0809; B01F 3/0819; B01F 11/0094; B01F 5/10; B01F
(Continued)

(56) References Cited

U.S. PATENT DOCUMENTS

| 8,147,619 B2 * | 4/2012 | Ackermann | B01J 19/008 134/168 R |
| 2010/0291639 A1 * | 11/2010 | Ackermann | B01J 19/008 435/105 |

FOREIGN PATENT DOCUMENTS

| DE | 10 2009 048 348 A1 * | 4/2011 | ............... F42D 3/00 |
| DE | 10 2010 004 319 A1 * | 7/2011 | ............... B08B 3/10 |

(Continued)

OTHER PUBLICATIONS

Machine Translation of DE 10 2009 048 348 A1.*
(Continued)

*Primary Examiner* — Daniel C McCracken

(57) ABSTRACT

7 different technical machines are explained for hydrodynamic cavitation generation in large scale. Also 4 chemical, processes are published which have are widely used. Machine 1 is a device for magnetic cavitation generation. Machine 2 is a device for cleaning applications with all relevant parts inside the vacuum container. Machine 3 is a cleaning machine with a vibration isolation sieve inside the liquid. Machine 4 is a machine with cavitation generation plates inside the liquid. Machine 5 is a laboratory and industrial mixing machine for containers with standardized dimensions. Machine 6 is a vibration table based cavitation generation machine with more than one plate inside liquid. Machine 7 is a vibration generation pipe with increased cavitation generation. The first process is cavitation biodiesel process. The second process is a cavitation polyester (PET) generating process. The third process is a cavitation wastewater treatment process. The fourth process is cavitation oil sands extraction process.

11 Claims, 18 Drawing Sheets

(51) Int. Cl.
| | |
|---|---|
| B01F 13/08 | (2006.01) |
| B01F 15/02 | (2006.01) |
| B01F 11/02 | (2006.01) |
| C12P 5/02 | (2006.01) |
| C02F 1/34 | (2006.01) |
| C10L 1/02 | (2006.01) |
| C10G 1/04 | (2006.01) |
| C07C 29/36 | (2006.01) |
| C07C 67/02 | (2006.01) |
| C08G 63/183 | (2006.01) |
| B01D 21/28 | (2006.01) |
| B01F 3/08 | (2006.01) |
| B01F 11/00 | (2006.01) |
| C07C 67/03 | (2006.01) |
| B01F 5/10 | (2006.01) |
| B01F 13/06 | (2006.01) |
| B01D 3/10 | (2006.01) |
| C02F 1/04 | (2006.01) |
| C10G 31/10 | (2006.01) |
| C10G 32/02 | (2006.01) |

(52) U.S. Cl.
CPC ............ *B01D 21/28* (2013.01); *B01F 3/0819* (2013.01); *B01F 5/10* (2013.01); *B01F 11/0077* (2013.01); *B01F 11/0094* (2013.01); *B01F 13/06* (2013.01); *B01F 13/0809* (2013.01); *B01F 15/0216* (2013.01); *B01J 19/00* (2013.01); *C02F 1/048* (2013.01); *C02F 1/34* (2013.01); *C07C 29/36* (2013.01); *C07C 67/02* (2013.01); *C07C 67/03* (2013.01); *C08G 63/183* (2013.01); *C10G 1/045* (2013.01); *C10G 1/047* (2013.01); *C10G 31/10* (2013.01); *C10G 32/02* (2013.01); *C10L 1/026* (2013.01); *C12P 5/02* (2013.01); *C12P 5/023* (2013.01); *B01F 2215/0036* (2013.01); *B01F 2215/0052* (2013.01); *B01F 2215/0088* (2013.01); *B01J 2219/085* (2013.01); *C02F 2303/04* (2013.01); *C10G 2300/1033* (2013.01); *C10L 2270/026* (2013.01); *Y02E 50/13* (2013.01)

(58) Field of Classification Search
CPC ............... 15/021;C02F 1/34; C10G 1/047; C10L 1/026; C08G 61/183; C12P 5/02
USPC ............... 261/DIG. 48; 435/167; 203/91; 208/391; 210/748.01; 366/108, 127; 528/274; 554/167
See application file for complete search history.

(56) References Cited

FOREIGN PATENT DOCUMENTS

| | | | | |
|---|---|---|---|---|
| DE | 10 2010 006 753 A1 | * | 8/2011 | ............ B01J 19/10 |
| DE | 10 2010 051 485 A1 | * | 5/2012 | ............ B01J 19/10 |
| DE | 10 2012 011 555 A1 | * | 12/2013 | ............ B01J 19/10 |

OTHER PUBLICATIONS

Machine Translation of DE 10 2010 004 319 A1.*
Machine Translation of DE 10 2010 006 753 A1.*
Machine Translation of DE 10 2010 051 485 A1.*
Machine Translation of DE 10 2012 011 555 A1.*

* cited by examiner

101

102

104

105

107

106

$$H_2O \longrightarrow X + (-OH)$$

$$(-OH) + C_{13}H_{18}O_2 \longrightarrow Y + CO_2$$

CAVITATION GENERATION MECHANISMS AND THEIR USE IN FERMENTATION AND WASTEWATER AND SAND CLEANING PROCESSES

CROSS-REFERENCE TO RELATED APPLICATIONS

Not Applicable

FEDERALLY SPONSORED RESEARCH

Not Applicable

SEQUENCE LISTING OR PROGRAM

Not Applicable

BACKGROUND OF THE INVENTION

1. Field of Invention

The field of the invention is the field of chemical and mechanical reaction technology.

2. Prior Art

Chemical reactions are overall used for converting substances. A relatively young field in the science of chemistry is the field of the sonochemistry. In sonochemistry acoustic waves are used for generating small bubbles inside a liquid which are collapsing rapidly a short time after they are created. Through the intensive collapse of these bubbles enormous pressures and temperatures are generated which are increasing chemical reaction rates. But the energy efficiency of this process is very low. Most of the acoustic energy dissipates unused inside the liquid. The patents or rather patent applications U.S. Pat. No. 8,147,619 B2 and DE102009048348A1 and U.S. Pat. No. 7,998,449 and DE102010006753A1 are unique sources for that physical effect.

In these papers the cavitation is generated through vertical oscillations of a liquid inside a vacuum container. If cavitation is produced with this method large cavities are generated therefore intensive collapses occur. But as this process generates cavitation very efficient it is still not used commonly in industrial practice.

The cavitation generating mechanism is clearly described in the above mentioned applications. In a few sentence described: A liquid is inside a not completely filled vacuum container, a vacuum pump is applied to generate a vacuum inside the vacuum container then external vibrators are used to oscillate the container vertically with more than 2 g. The effect is the following while the liquid is accelerated downwards the gravitation force is not strong enough to follow the container bottom or some part of the liquid so large cavities inside the liquid occur which will shortly collapse after the liquid is accelerated upwards again. This technical alignment has some disadvantages which will be mentioned later.

Wastewater cleaning consists in the most industrial countries of three stages which are mechanical cleaning, biological cleaning and chemical cleaning.

The mechanical cleaning uses a few conventional methods. These are up concentration, removing large objects with sieves or sedimentation in tanks and skimming.

Biological cleaning is used to degrade biological content of the sewage. And therefore aerobic biological processes are mainly used. The bacteria and microorganisms convert the waste into non harmful substances.

Chemical cleaning is mostly the last step in the wastewater treatment process. For example strongly acidic or alkaline wastewater are toxic for most of the organism so the wastewater have to be neutralized before it is sent to the rivers.

This was only a very short explanation of wastewater treatment there are much more processes used (for example Activated Slurry process). For further information have a look at the literature or books available.

Ultrasonic application for wastewater treatment is like sonochemistry a new field with create scientific interest.

In "Application of Ultrasonic Technology for Water and Wastewater Treatment" from A H Mahvi in Iranian J Publ Health, Vol. 38, No. 2, 2009 on pages 1-17 ultrasonic processes are mentioned and their use for wastewater treatment.

In "Industrial wastewater treatment using hydrodynamic cavitation and heterogeneous advanced Fenton processing" by Anand Chakinala in Chemical Engineering Journal Volume 152, Issues 2-3 from 15 Oct. 2009 on Pages 498-502 a chemical process is used which generates cavitation hydro dynamically and not with soundwaves.

Also ultrasonic equipment is available for fermentation increase in biogas plants such devices can be also used in wastewater treatment facilities to increase the output of activated slurry or fermentation biogas production.

In the above mentioned process of mechanical wastewater cleaning large amounts of dirty sands are produced which have to be sometimes further processed. Also as accidents with chemicals occur and it happens that oil or chemicals contaminate the sand. Another process were sands cleaning is used is in the oil sands mines in Canada. In all the mentioned applications the process is similar; the sand is mixed with hot water or a solvent to remove the chemicals, sands etc.

In all the above mentioned prior art processes and applications are some disadvantages which are very similar.

(a) The cavitation generated with the process described in U.S. Pat. No. 8,147,619 B2 has the problem that the cavitation is at the bottom of the table very intensive and in the middle of the liquid not so strong.

(b) The cleaning mechanism described in U.S. Pat. No. 8,147,619 B2 is not as effective as it could be because of the fact that the cavitation is not directly generated at the object which has to be cleaned.

(c) If someone wants to upscale the process described in U.S. Pat. No. 8,147,619 B2 he has the problem that it is very complicated to get powerful enough electric vibrators for such a device.

(d) In the nanoparticle generation process described in U.S. Pat. No. 7,998,449 the cavitation is powerful enough to produce the carbon nanoparticles or other nanoparticles but a lot of time is needed which limits the potential or output.

(e) Ultrasonic equipment for wastewater treatment is very expensive.

(f) Ultrasonic waves cannot penetrate the wastewater very deep they have the problem that they are absorbed in first few centimeters. So the construction of large wastewater treatment plants with such a technology is very expensive.

(g) Because of the limitations mentioned in (f) the output cannot be very large. So a lot of devices are needed to get the result.

(h) As described in "The Energy Efficiency of Formation of Photons, Radicals, and Ions during Single Bubble Cavitation" from Suslick et al. in Nature 418 on pages 394-297 from 25 Jul. 2002 the energy efficiency of acoustic cavitation is quite low.

(i) Large stirring machines used in wastewater treatment plants have the problem that it is for them impossible to generate a very good micro fluidity. Micro fluidity means if you have a very large stirrer the flow in a stirring vessel follows the stirrer but if the stirrer is big the turbulences generated with the stirrer are also big for a perfect mixing a lot of turbulence and very small turbulence is needed.
(j) Insufficient mixing causes limitations in the efficiency of all chemical and biological cleaning steps.
(k) In oil sands cleaning large amounts of water and solvents and energy are used which generate a lot of wastewater and costs.

BACKGROUND OF THE INVENTION

Objects and Advantages

Because of the fact that all mentioned problems have similar occurrences. Most of them can be solved with use of a new mixing or chemical reaction technology which is able to increase chemical reactivity. But therefore the in U.S. Pat. No. 8,147,619 B2 described process and machines have to be improved that they are capable for processing larger volumes
(a) The invention solves the problem of the irregular cavitation generation at the bottom of the vibration table
(b) The cavitation generation is now directly at the object which has to be cleaned.
(c) Upscaling the process described in U.S. Pat. No. 8,147,619 B2 can now be easily done.
(d) Nanoparticle generation is greatly increased because of the fact, that the cavitation is much stronger.
(e) No ultrasonic equipment is needed only cheap standard mechanical equipment.
(f) Because of the fact that no ultrasonic waves are used the cavitation generation mechanism penetrates completely the liquid.
(I-j) Because of the (f) the mixing is very effective even in the micrometer scale.
(k) It is well known that cavitation can emulsify oil and water and also well known that cavitation can be used for cleaning applications so the if the cavitation generation mechanism is applied to oil sands it is obvious that the sand can be cleaned or the oil can be extracted.

SUMMARY

The invention consist mainly on the following technical process. Inside a liquid, which is inside a vacuum container, particles are excited to vertical vibrations. Through this vertical excitations small cavities are generated at the object which are immediately collapsing. Through that collapse enormous pressures and temperatures are generated, which increases chemical reactivity. 7 different technical machines and 4 different chemical processes are now detailed described.

DRAWINGS

Reference Numerals

Figure 5:
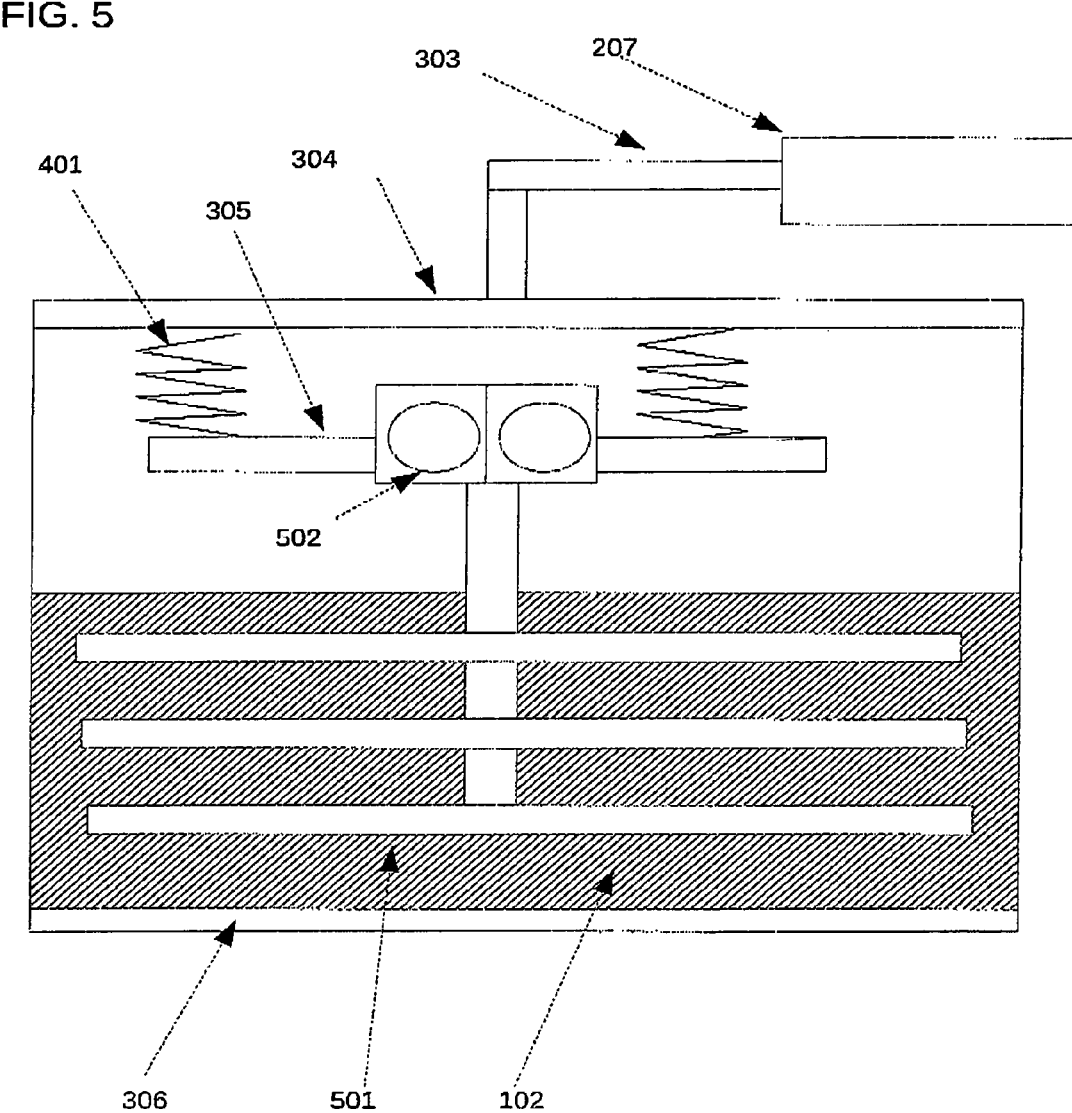
FIG. 5 shows a cavitation generation machine with cavitation generation plates inside the liquid.
Figure 7A:
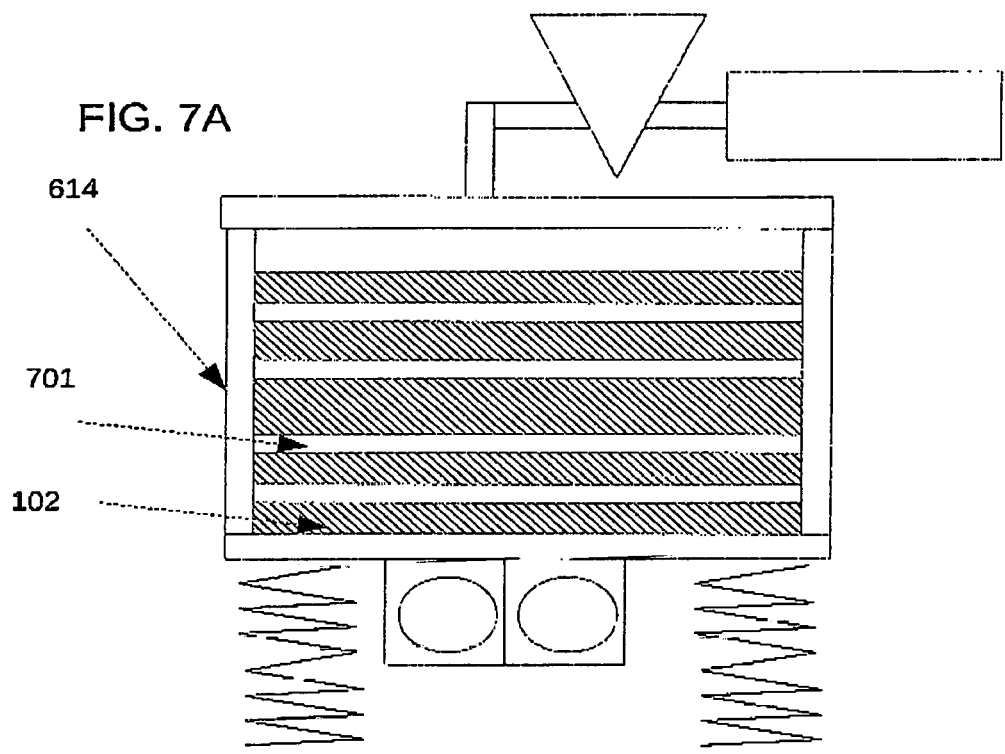
FIG. 7A to 7D show a vibration table based cavitation generation machine with more than one plate inside liquid.
Figure 7B:
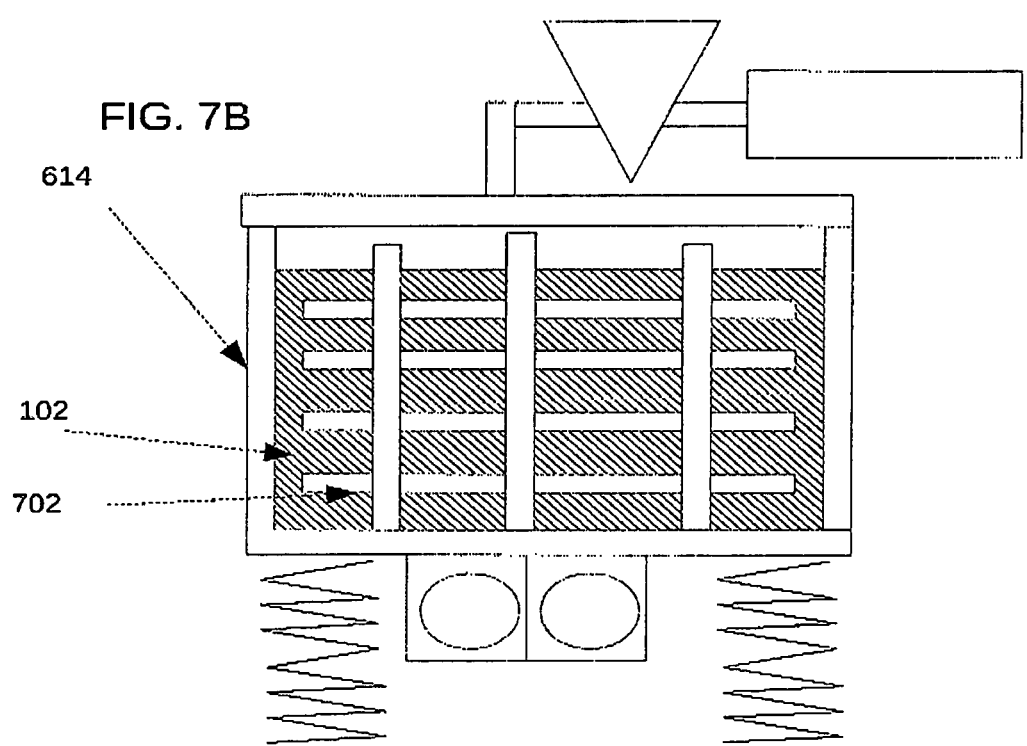
Figure 7C:
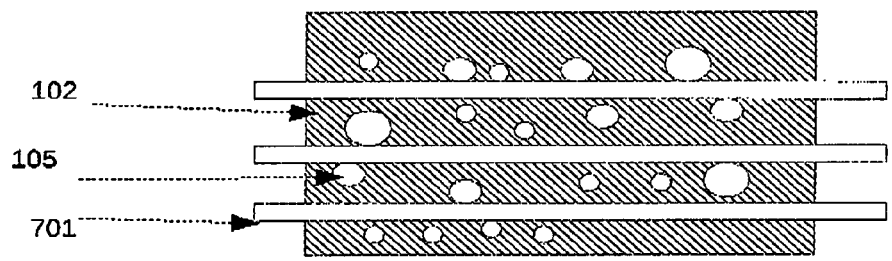
Figure 7D:
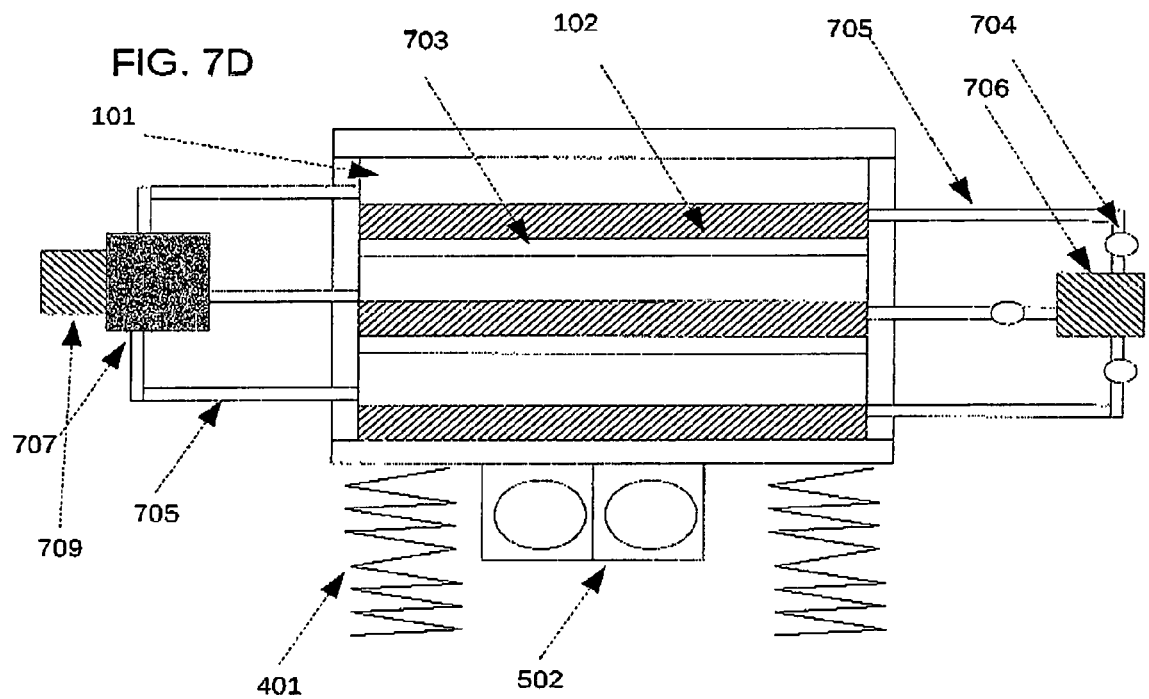
Figure 8A:
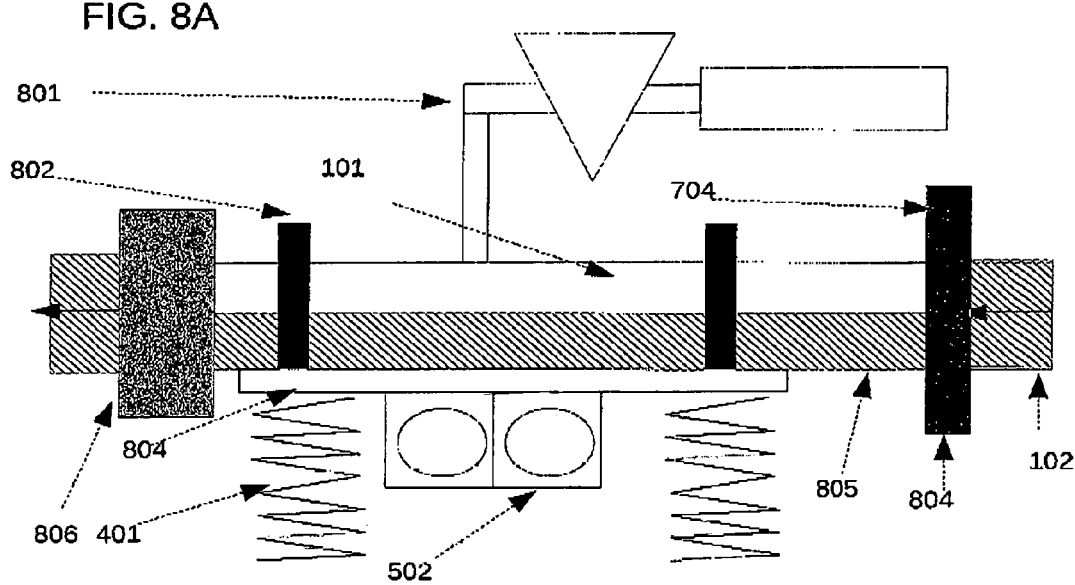
FIG. 8A to 8C show a vibration generation pipe with increased cavitation generation.

101 Vacuum
102 Liquid
103 Upwards Direction
104 Vacuum gap
105 Cavitation bubble
106 Collapsing bubble and shock waves
107 Downwards direction
201 Electric magnet
202 Ac Voltage and Current Power Supply
203 Vacuum container
204 Object
205 Particles
206 Cavitation bubble
207 Vacuum pump
301 Sieve
302 Rubber buffer
303 Vacuum connection
304 Cover
305 Mounting plate
306 Vacuum container
307 External electric vibrators
401 spring
402 Damper
501 plates with holes
502 Electric vibrators
601 Separator
602 Vibration table
603 Rack
604 Adapter for containers with standardized connections
605 Cover connected with hinge
606 Container with standardized connections
607 mounting plate with hole
608 Lock for the cover
609 Height adjustable hinge
610 Rubber bumper with side restraints
611 Vacuum container with cover
612 Vibration protection adapter for standard containers
613 IBC container
614 Vibration table with vacuum container and vacuum system
615 IBC adapter
616 Barrel with standardized dimensions
617 Adapter for barrel with standardized dimensions
618 Enlarged view of the vacuum adapter and standard container 619 Standard container
620 Vacuum adapter
621 flow barrier
622 air flow
623 Enlarged view of 610
624 side restraints
701 plates with holes
702 Connected plates with holes
703 Plate
704 Metering valve
705 Tube
706 Tube filled with a liquid
707 Pump
708 Vacuum container
709 Tube with liquid
801 Vacuum system with separator and pump
802 Pipe mounting
803 Vibration plate
804 Control for metering valve
805 Vacuum pipe
806 Fluid pump
807 Valve output
808 Valve input
901 Methanol with catalyst
902 Vegetable oil
903 Metering pump
904 Device of FIG. 8a
905 Centrifugal separator
906 Glycerin
907 Biodiesel
908 Ethylene glycol with catalyst
910 Terephthalic acid
911 Esterification reactor (a device of FIG. 5)
912 Unused chemicals
913 Separation vessel
914 Feed for separation vessel
915 Waste and water
916 Recovered feed
917 Feed for polycondensation reactor
918 Device of FIG. 5
919 Liquid
920 Pet plastic
921 Ethylene glycol
922 Reaction tank
1001 Wastewater
1002 Stirrer
1003 Aeration tank
1004 Device of FIG. 7D
1005 Pipe
1006 Longer pipe
1007 Bubbles of air
1008 Sludge
1009 Sludge digestion
1010 Methane gas
1011 Fermentation vessel
1012 Sludge in fermentation vessel
1101 Microorganism
1102 Organic waste
1103 Destroyed organic wastes
1104 Collapsing bubble with shock waves
1201 Mined oil sands
1202 Device of FIG. 8a
1203 Crusher
1204 Unused rest
1205 Slurry
1206 Cavitated slurry
1207 Oil
1208 Water
1209 Sand and dirt

DETAILED DESCRIPTION OF THE DRAWINGS

Figure 1A:
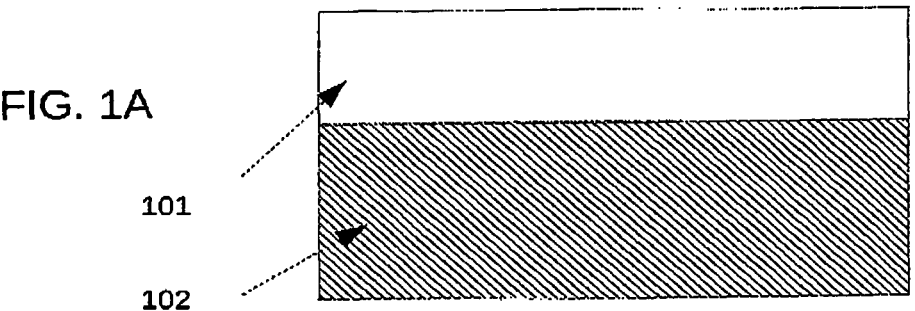
FIGS. 1A to 1D show the physical effect.

FIG. 1 shows different steps of a vertical acceleration of a liquid, which is inside a vacuum container FIG. 1A shows a liquid (102). Above the liquid is a vacuum (101).

Figure 1B:
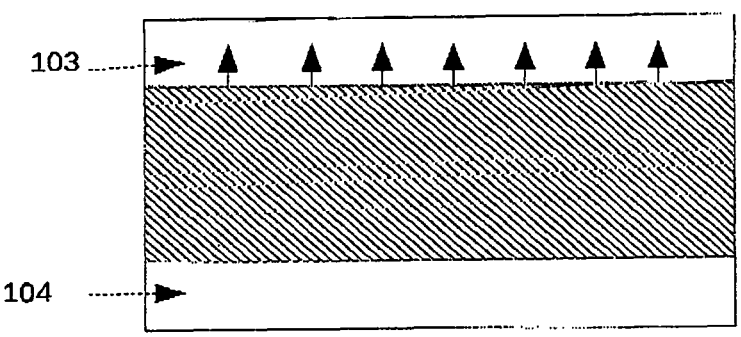

FIG. 1B shows the liquid, which is accelerated in upwards direction (103). At the bottom of the liquid is also a vacuum gap (104)

Figure 1C:
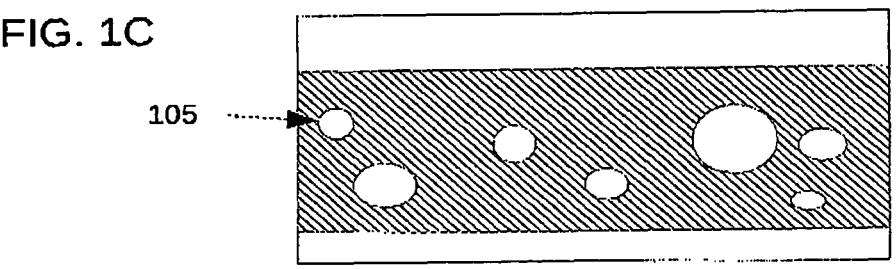

FIG. 1C shows the liquid at a different point of the acceleration where cavitation bubbles are generated inside the liquid (105).

Figure 1D:
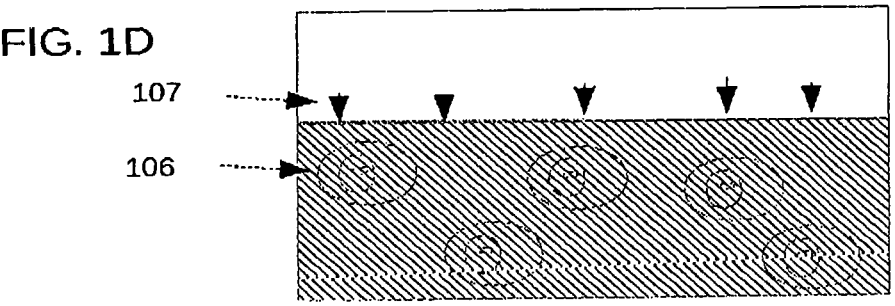

FIG. 1D shows collapsing cavitation bubbles with shock waves (106) during the acceleration in downwards direction (107).

Figure 2:
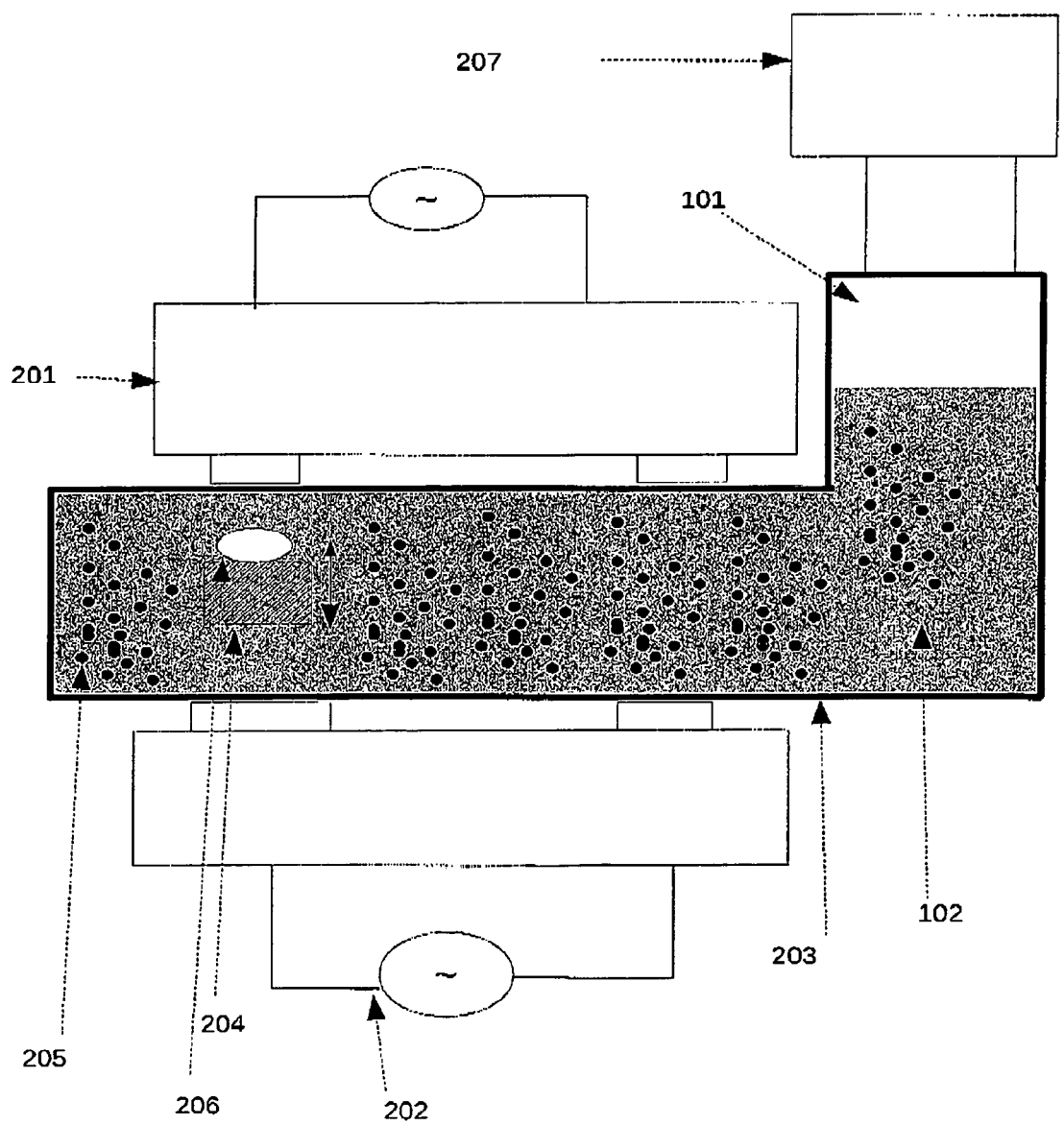
FIG. 2 shows an apparatus with magnetic cavitation generation.

FIG. 2 shows a vacuum pump (207) connected to a vacuum container (203) in which is a liquid (102). Inside the liquid (102) are particles (205) and objects (204). The vacuum container (203) is not complete filled with the liquid (102) there is also a vacuum (101).

At the top of the vacuum container (203) is an electric magnet (201) mounted also at the bottom of the container. The two electric magnets (201) are connected with two ac voltage and current power supplies (202).

At the object (204) cavitation bubbles (105) are.

Figure 3:
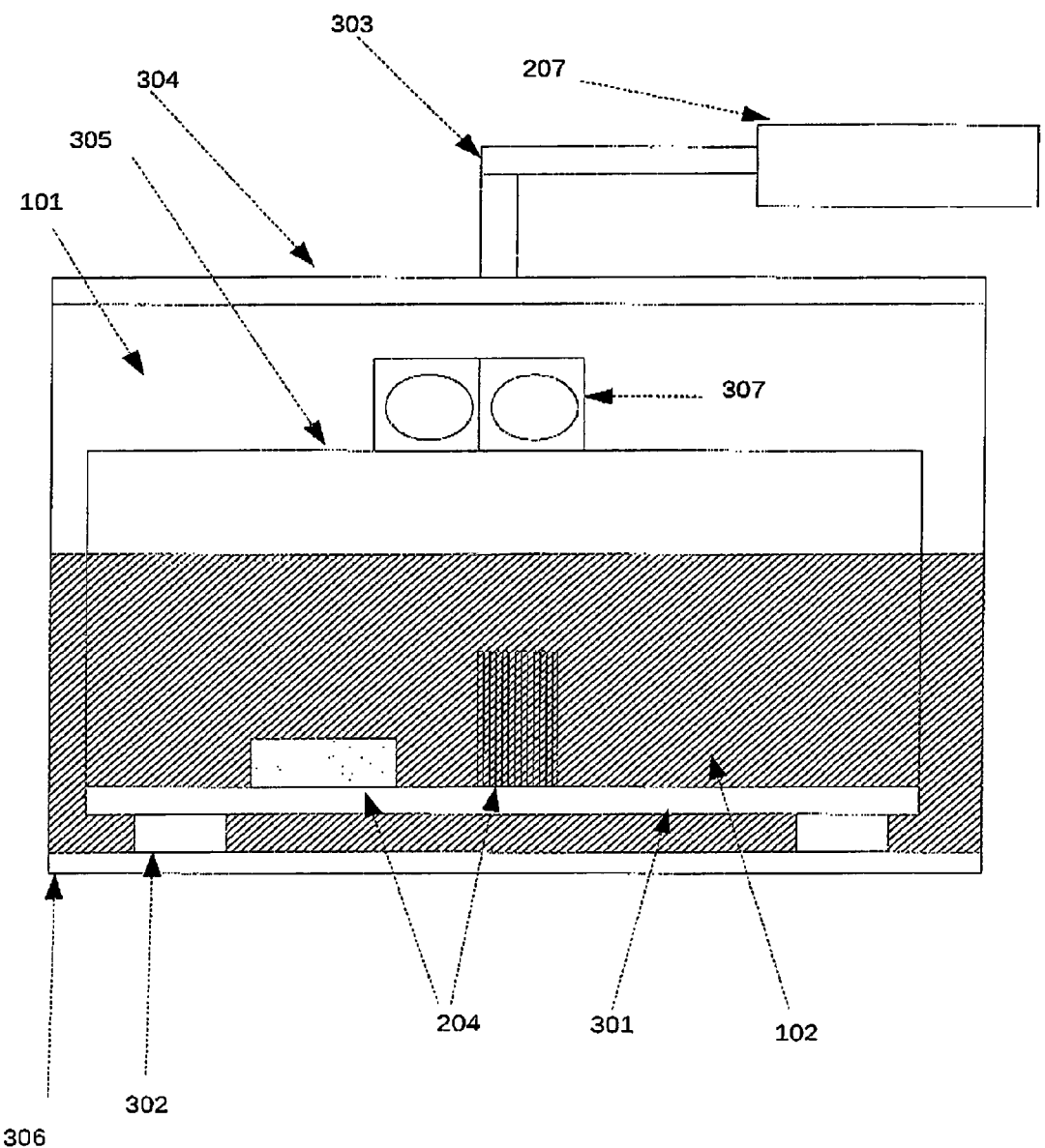
FIG. 3 shows a cleaning machine with all relevant parts inside the vacuum container.

FIG. 3 consists of a vacuum container (203), which is connected through a cover (304) and a vacuum connection (303) to a vacuum pump (207).

Inside the vacuum container (203) are a liquid (102) and a vacuum (101). At the bottom of the vacuum container (203) a sieve (301) is mounted via rubber buffers (302) to the vacuum container (203). Two objects (205) are on the sieve (301). The sieve is connected to a mounting plate (305) which has two external electric vibrators (307). The objects are fortified to the sieve.

Figure 4:
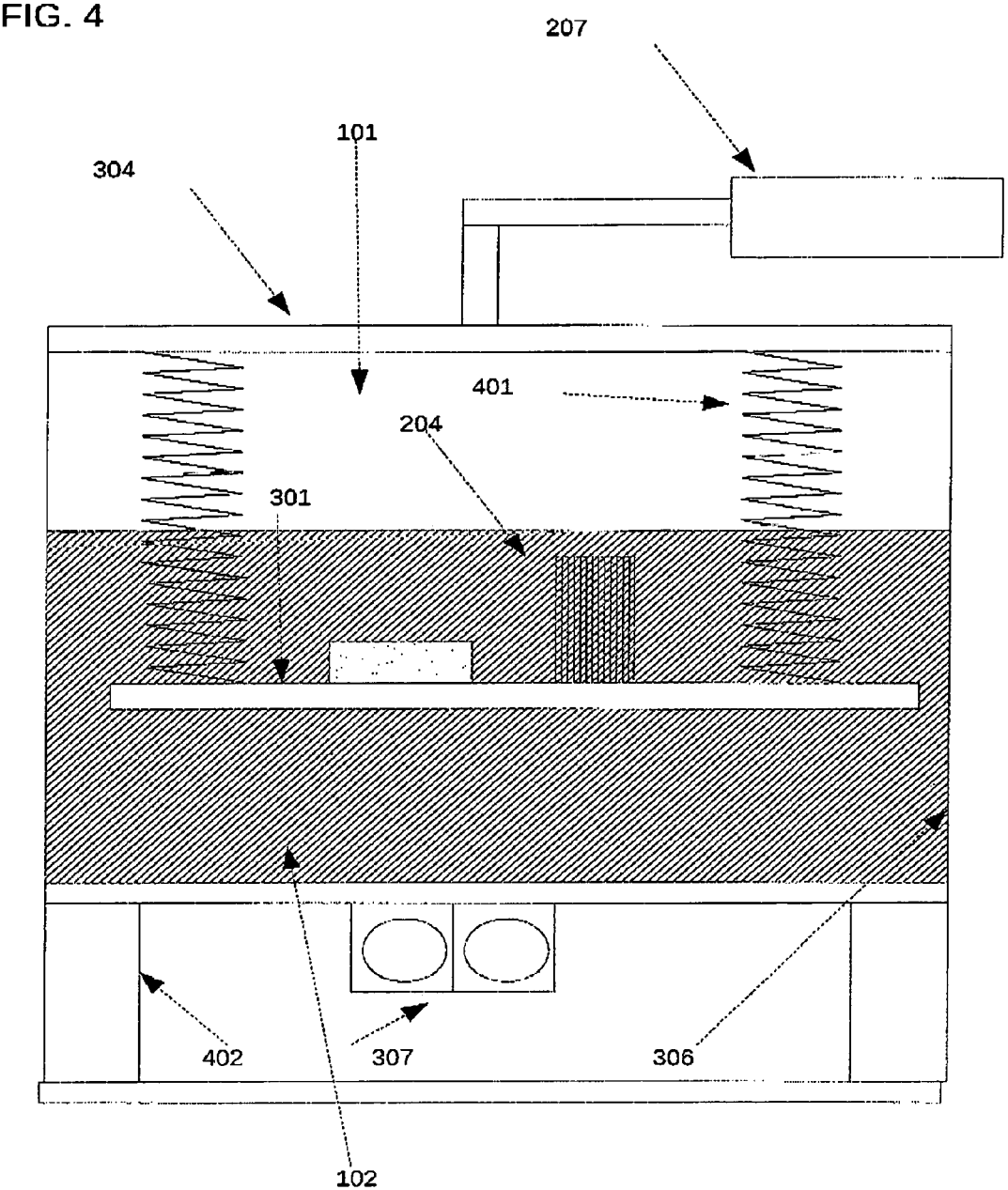
FIG. 4 shows a cleaning machine with a vibration isolation sieve inside the liquid.

FIG. 4 shows a vacuum pump with vacuum connection (303) connected to a cover (304), which is on a vacuum container (203). Inside this vacuum container (203) is sieve (301), which is connected to the cover (304) via spring (401). There are objects (204) on the sieve (301). The vacuum container (203) is partly filled with a liquid (102) and a vacuum (101). Two external electric vibrators (307) are mounted outside at the bottom of the vacuum container (203). Also dampers (402) are mounted outside at the bottom of the vacuum container (306).

FIG. 5 shows a vacuum pump (207) connected via a vacuum connection (303) to a cover (304) of a vacuum container (303). Two electric vibrators (307) are connected via a mounting plate (305) and springs (401) to the cover (304). Three plates with holes (501) are connected to the mounting plate (305) and the electric vibrators (502). The Vacuum container is partly filled with a liquid (102).

Figure 6A:
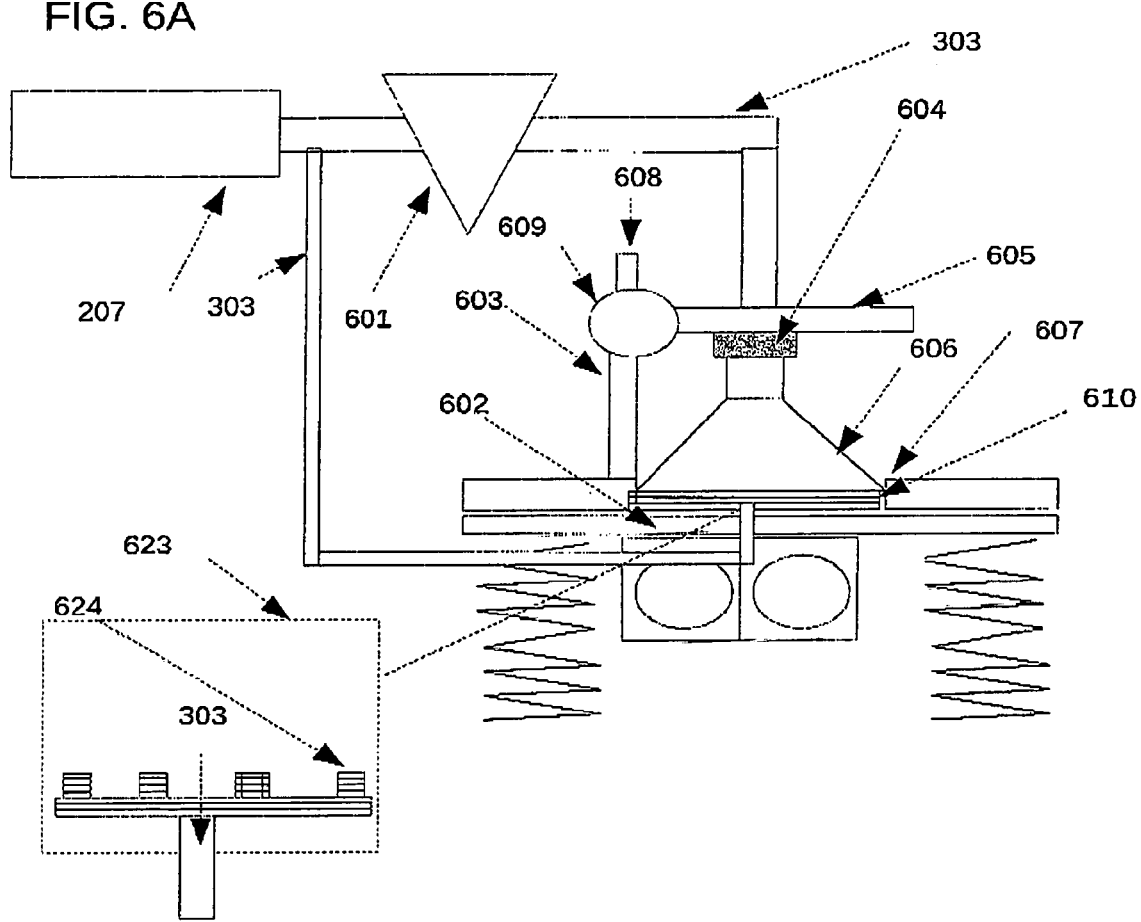
FIG. 6A to 6E show a three component-mixing machine for containers with standardized dimensions.

FIG. 6A show a vacuum pump (207) connected in fluid communication with a separator (601), which is connected via vacuum connection (303) to a cover which is connected to a hinge (605). The height adjustable hinge (609) is connected to a rack (603) which is mounted to a mounting plate with hole (607). There is a lock for the cover (608) as part of the hinge (609). A container with standardized dimensions (606) stands in a holes of a mounting plate with hole (607). The mounting plate with hole (607) is mounted on a vibration table (602). The container with standardized dimensions (606) is connected via an adapter for containers with standardized connections (604) through the cover connect with hinge (609) to the vacuum connection (303). At the bottom of the container (606) is a rubber bumper with side restraints (610). The container (606) stands in the rubber bumper with side restraints (607). There is a vacuum connection (303) from the rubber bumper with side restraints (607) to the vacuum pump (207). An enlarged view of the Rubber bumper with side restraints (607) is at the left (623). It shows clearly that the three are side restraints (624) and a vacuum connection (303) in the middle of the bumper (610).

Figure 6B:
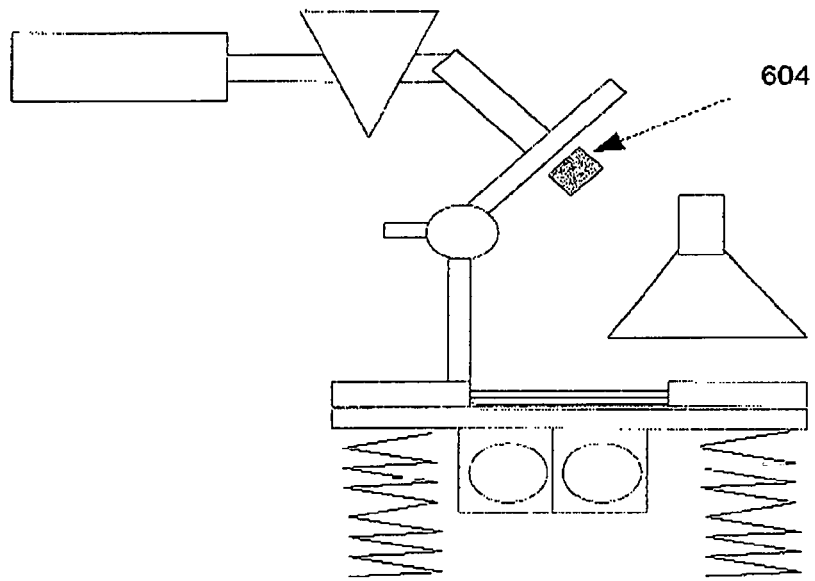

FIG. 6B shows the opened machine.

Figure 6C:
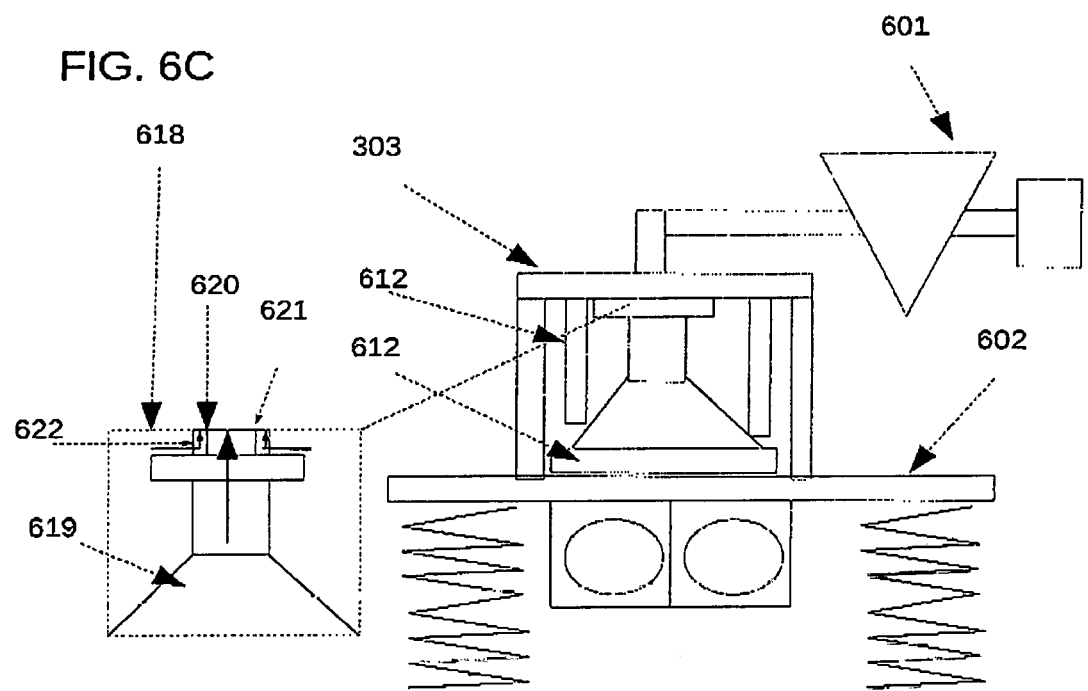

FIG. 6C shows a vacuum container (303) with cover mounted on a vibration table (602) and the cover connected to a vacuum system with separator (601). Inside the vacuum container (303) are vibration protection adapter for standard dimensions (612) and (612) protecting a standard container.

There is an enlarged view (618) of the vacuum adapter (620) and the standard container (619). There is an air flow (622) from the standard container (619) and from the left and right of the vacuum adapter (620).

Figure 6D:
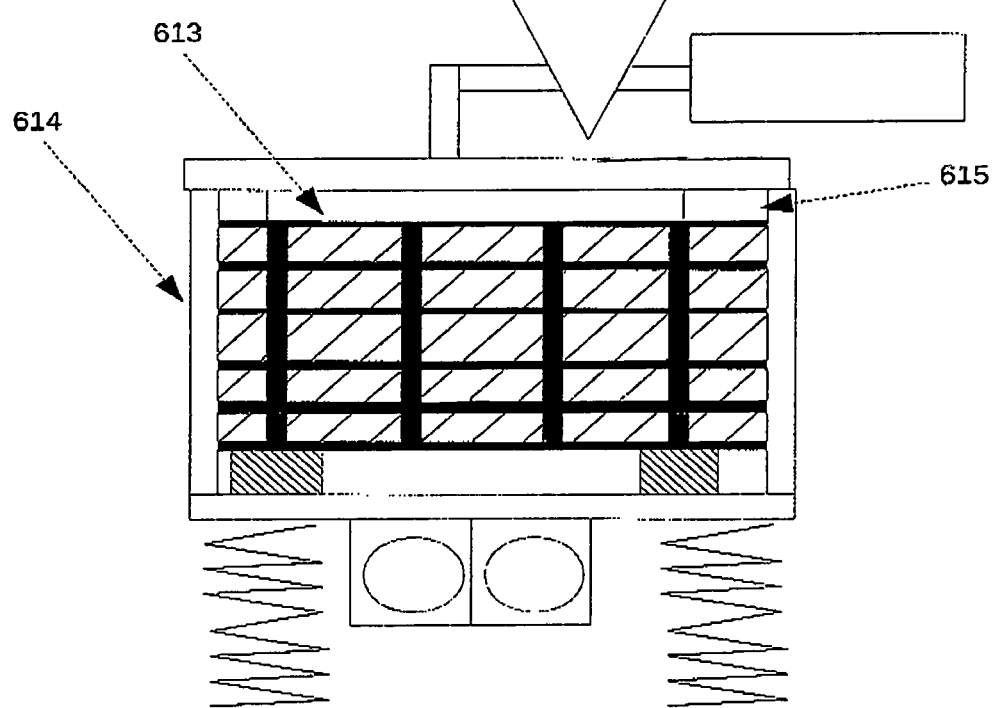

FIG. 6D shows a similar device as FIG. 6C a vibration table with vacuum container and vacuum system (614) but larger and optimized for an IBC container (613) which is widely used in chemical industry. There are IBC adapters (615) constructed for generating a connection between the vacuum system (614) and the IBC container (613).

Figure 6E:
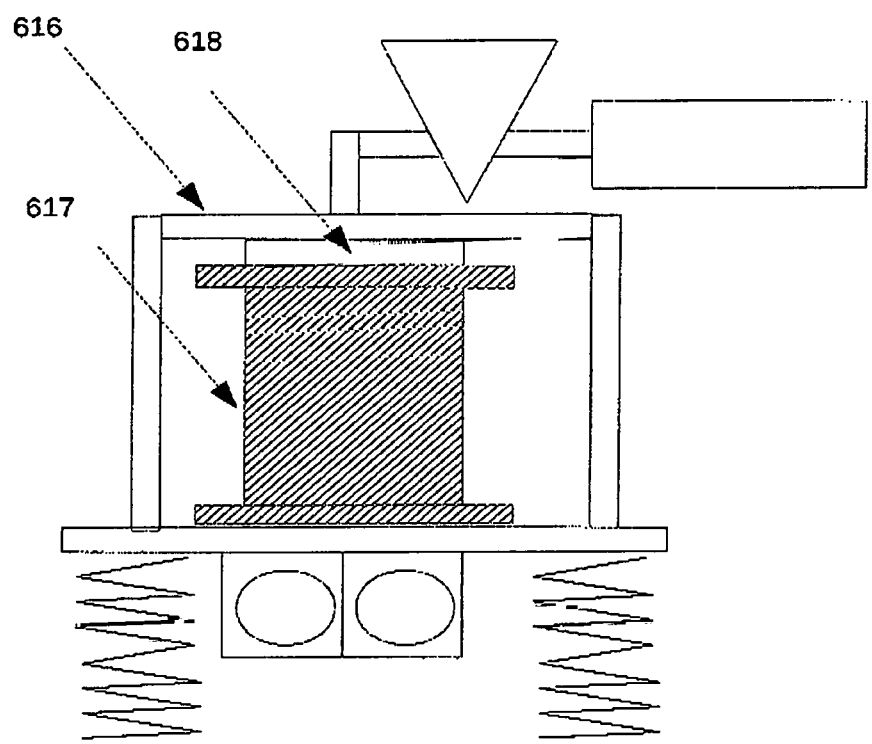

FIG. 6E shows a barrel with standardized dimensions (617) which are connected via adapter for barrel with standardized dimensions (618) to a vibration table with vacuum container and vacuum system.

FIG. 7A shows a vibration table with vacuum container and vacuum system (614) which has four plates with holes (701) mounted horizontally inside the container. The container is filled partly with a liquid (102).

FIG. 7B shows a vibration table with vacuum container and vacuum system (614) which is partly filled with a liquid (102) and inside the liquid (102) are connected plates with holes (702). The plates are not connected to the container (614).

FIG. 7C shows a liquid (102) in which cavitation bubbles (105) are generated at the plates with holes (701).

FIG. 7D shows a vacuum container (207) connected with two electric vibrators (502) and standing on four springs (401). At the left side of the vacuum container (207) are three inputs of three tubes (705) each of them has a metering valve (704) which is connected to a tube filed with a liquid (706). Inside the vacuum, container (207) are three plates (703) dividing the vacuum container (207) into three different parts. Each one part is partly filled with the liquid (102) and a vacuum (101). At the right side of the vacuum container (207) three tubes are connected. All three tubes (705) are connected at the end to a fluid pump (707) which is mounted on a tube with the liquid (709).

FIG. 8A shows a vacuum pipe (805) mounted via two pipe mountings (802) on a vibration plate (804) which is connected with four springs (401) and two electric vibrators (502). At the left end of the vacuum pipe (805) is a fluid pump (806) at the right end of the pipe is metering valve (704) with a control (804). Right from the valve (704) flows the liquid (102) into the vacuum pipe (805). The vacuum pipe (805) is not completely filled with the liquid (102) there is also a vacuum (101). At the top of the vacuum pipe (805) is a vacuum system with separator and pump (801) connected in fluid communication with the vacuum pipe (805).

Figure 8B:
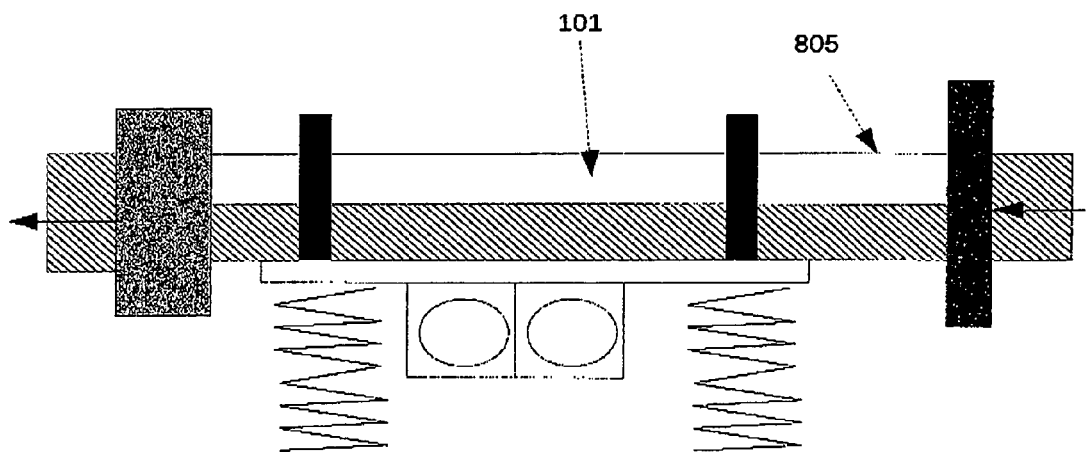

FIG. 8B shows the same device as FIG. 8A but without a vacuum system. The pipe is also not completely filled with the liquid.

Figure 8C:
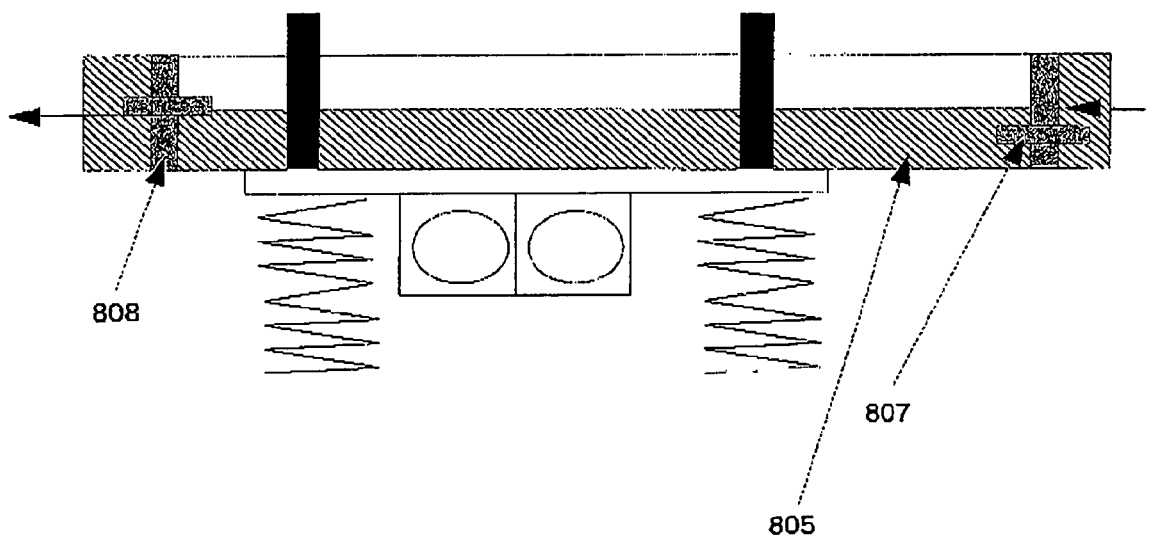

FIG. 8C shows the same device as FIG. 8B but with at the left end of the vacuum pipe (805) a valve output which is higher than the valve input (807) at the right side of the vacuum pipe (805).

Figure 9A:
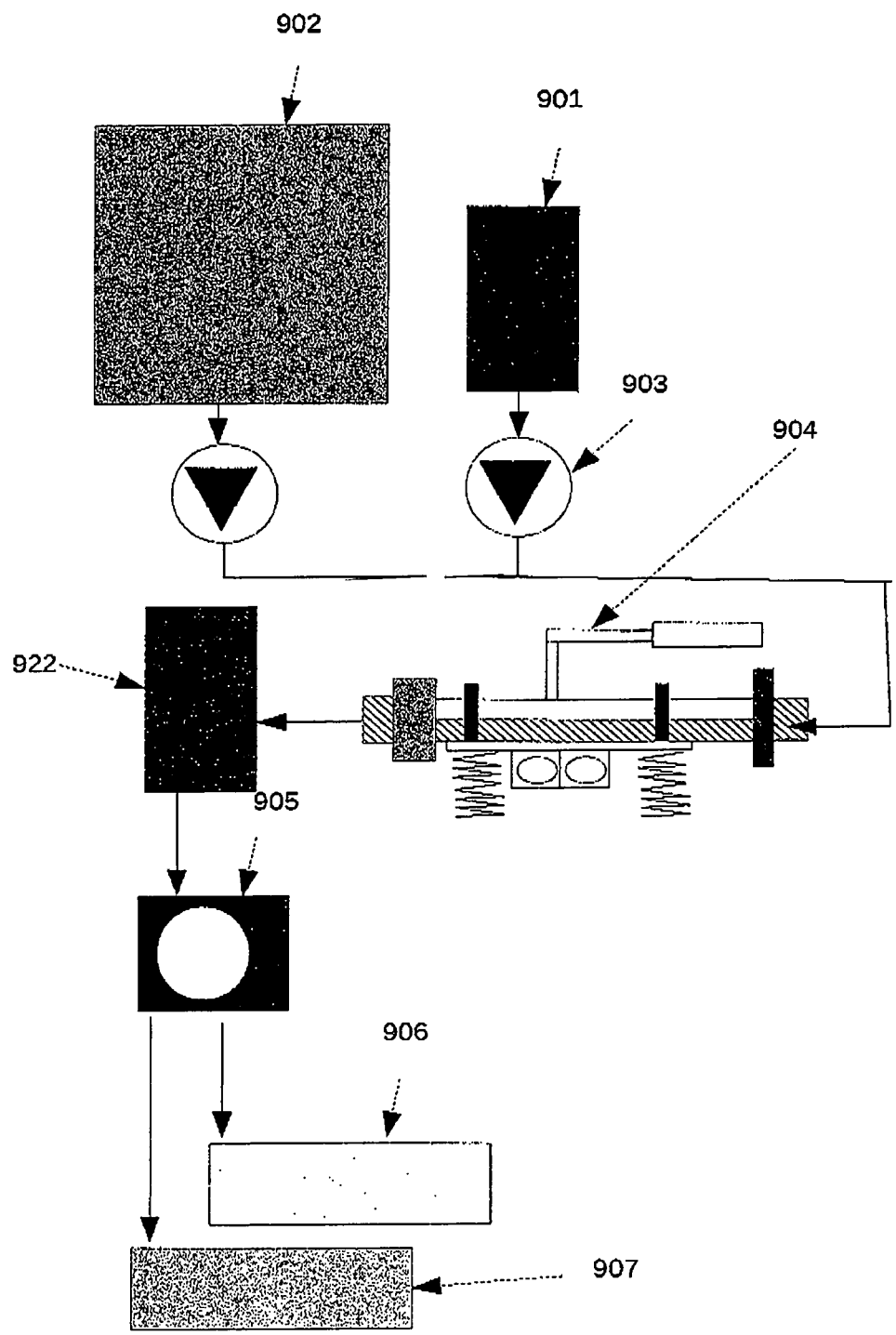
FIG. 9A shows a flow diagram of a biodiesel process.

FIG. 9A shows a biodiesel manufacturing process flow diagram. It starts with a tank filled with methanol and a catalyst (901) this tank is connected to a metering pump (903) which is connected in fluid communication to a device of FIG. 8A (904). Also another tank filled with vegetable oil (902) is connected to a metering pump (903) which is also connected in fluid communication to the device of FIG. 8A (904). The device of FIG. 8A (904) is on the left side connected in fluid communication with a reaction tank (922) which is in connection in fluid communication with a centrifugal separator (905) which separates the gylcerine (906) from the biodiesel (907).

Figure 9B:
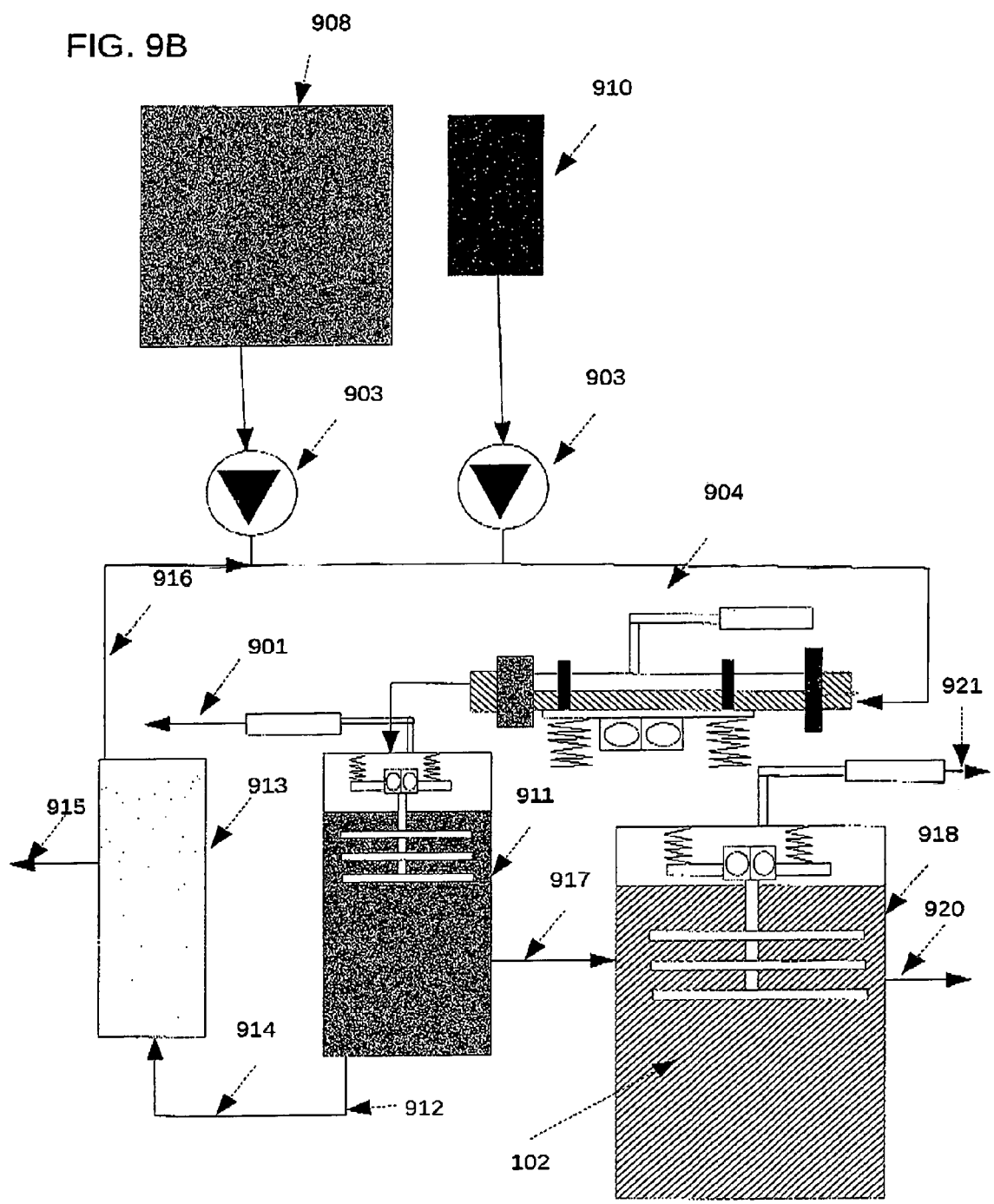
FIG. 9B shows a flow diagram of a polyester (PET) generation process.

FIG. 9B shows a tank with ethylene glycol with a catalyst (908) and a tank with terephalic acid (910). Both tanks are connected in fluid communication with two different metering pumps (903). The pumps are connected in fluid communication with a device of FIG. 8A (904). The left end of the device of FIG. 8A is connected in fluid communication with an esterification reactor (911). The esterification reactor (911) is a device of FIG. 5 and also connected to a device of FIG. 5 (918) in which the feed for the polycondensation reactor (917) flows. The device of FIG. 5 (918) is partly filled with a liquid (102). The outgoing result from the device of FIG. 5 (918) is the pet plastic (920). The other flow from the esterification reactor (911) are unused chemicals (912) which are the feed for the separation vessel (914). The separate vessel (913) has two outgoing flows one is waste and water (915) the second one is recovered feed (916). There are two flows from the two vacuum pump of the devices of FIG. 5 the first one is methanol (901) and the second one is ethylene glycol (921).

Figure 10A:
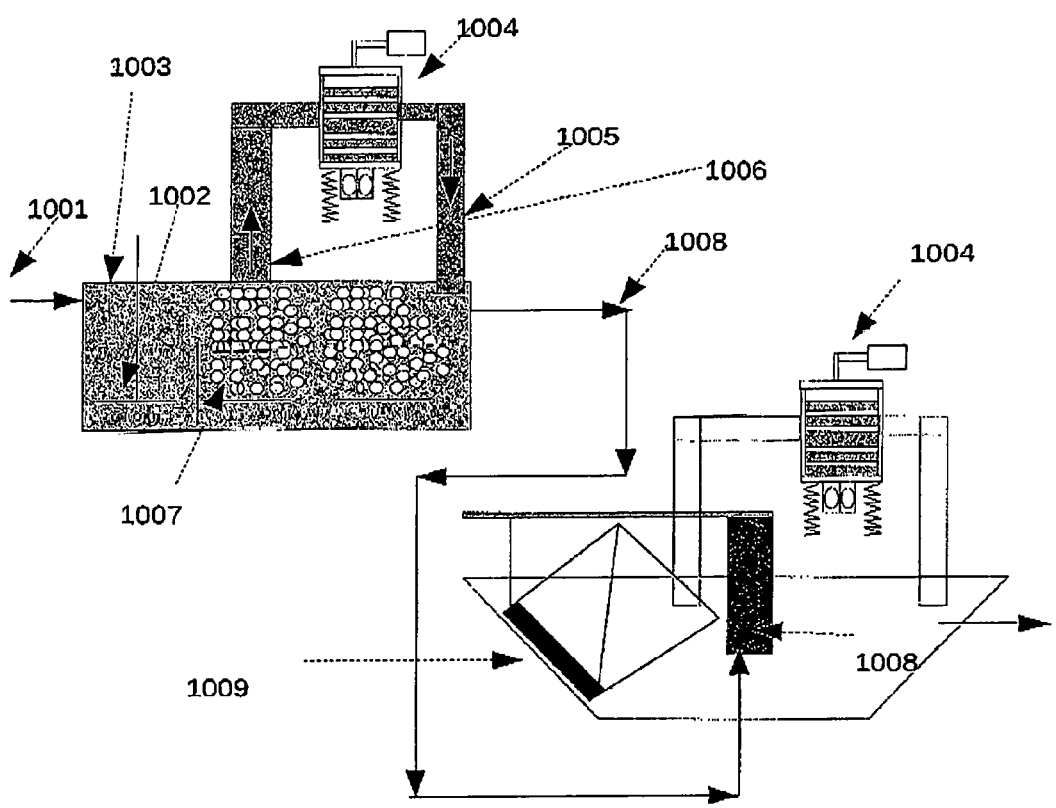
FIG. 10 A to 10B show a part of the wastewater treatment process in a normal standard wastewater treatment plant.

FIG. 10A shows an aeration tank (1003). At the left end of the aeration tank (1003) an inflow of wastewater (1001) flows into the tank. A stirrer (1002) in the aeration tank is in the left part of the tank. In the rest of the aeration tank (1003) are bubbles of air (1007). Because of the fact that the aeration tank (1003) is open a device of FIG. 7D (1004) is mounted at the side and outside of the tank (1003). Two pipes a longer one (1006) and a smaller one (1005) are connected in fluid communication with the tank and the device of FIG. 7D (1004). The flow diagram shows an outgoing output from the aeration tank (1003) a sludge (1008) which flows into a sludge digestion (1009) as feed sludge (1008). To the sludge digestion device (1009) is also a device of FIG. 7D connected in fluid communication. The output at the left side of the sludge digestion is the cleaned water.

Figure 10B:
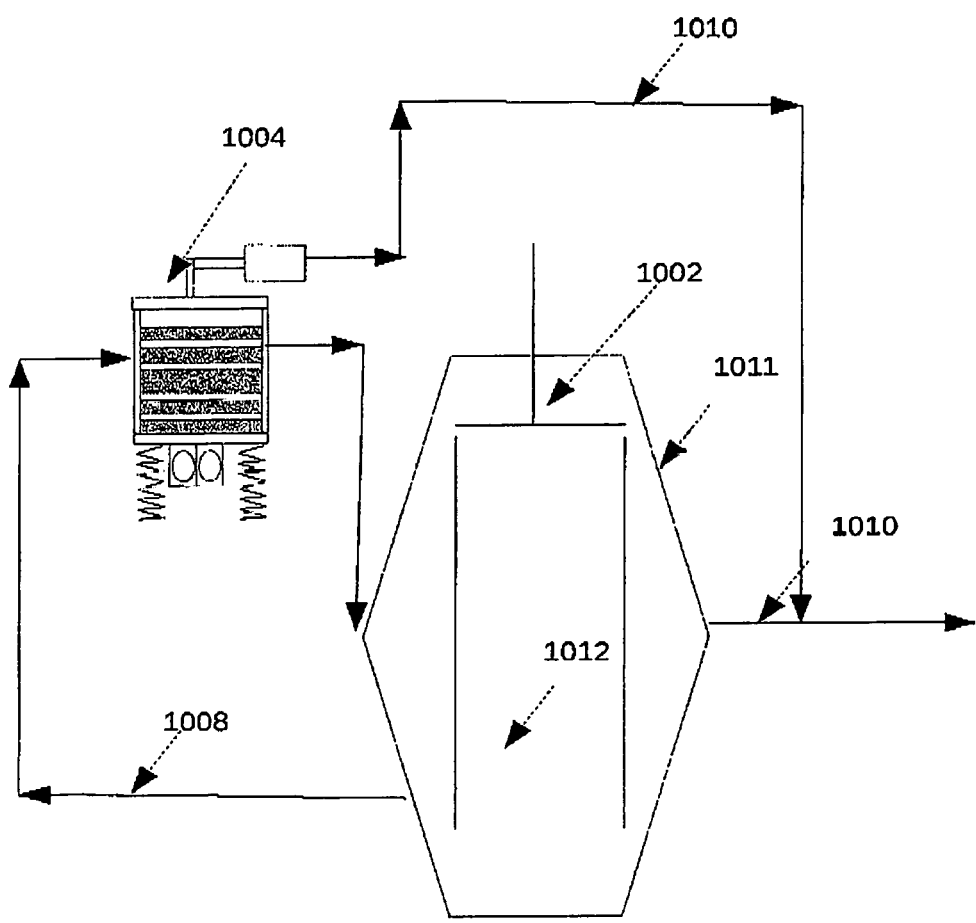

FIG. 10B shows what happens to the sludge from the sludge digestion device.

As the central part of the drawing there is a fermentation vessel (1011) in which is a stirrer (1002) at the top of the vessel. The vessel (1011) is filed with sludge (1012). A device of FIG. 7D is at the left side connected in fluid communication with the fermentation vessel (1011). There is a flow of sludge (1008) from the vessel (1011) to the device (1004) and backwards. Also there is a flow from the left side of the vessel (1011) and the device (1004) of, methane gas (1010).

Figure 11A:
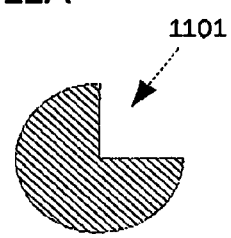
FIG. 11A to 11F show the physical and chemical effects of wastewater treatment claimed by this invention.

FIG. 11A shows a microorganism (1101) and a cavitation bubble (105) at some organic waste (1102). It is the first scene in the process of cavitation increased biological reactions.

Figure 11C:
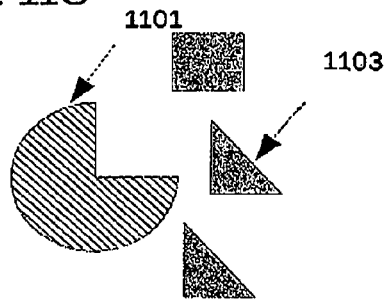
Figure 11B:
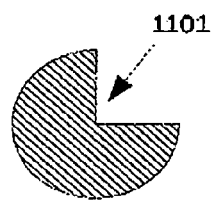

FIG. 11B shows a microorganism (1101) and a collapsing cavitation bubble (1104) collapsing at some organic waste (1102). It's the second scene as the cavitation bubble is collapsing.

FIG. 11C shows a microorganism (1102) and destroyed organic waste (1103). It is the third scene.

Figure 11D:
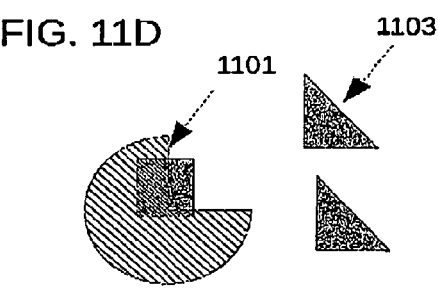

FIG. 11D shows a microorganism (1101) eating the destroyed organic waste (1103). It is the fourth scene and last scene.

Figure 11E:
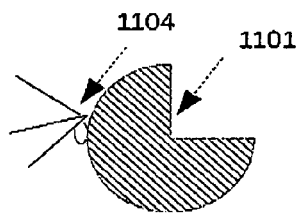

FIG. 11E shows a collapsing cavitation bubble (1104) destroying a microorganism (1101).

Figure 11F:
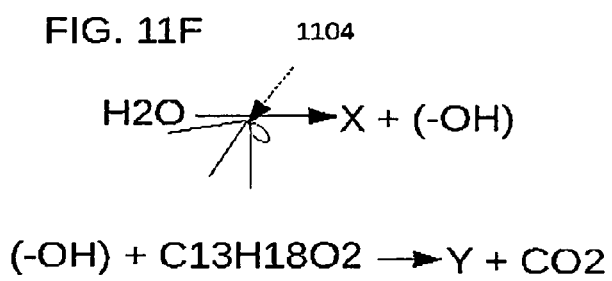

FIG. 11F shows a chemical reaction schema where H2O is changed with a collapsing cavitation bubble (1104).

Figure 12:
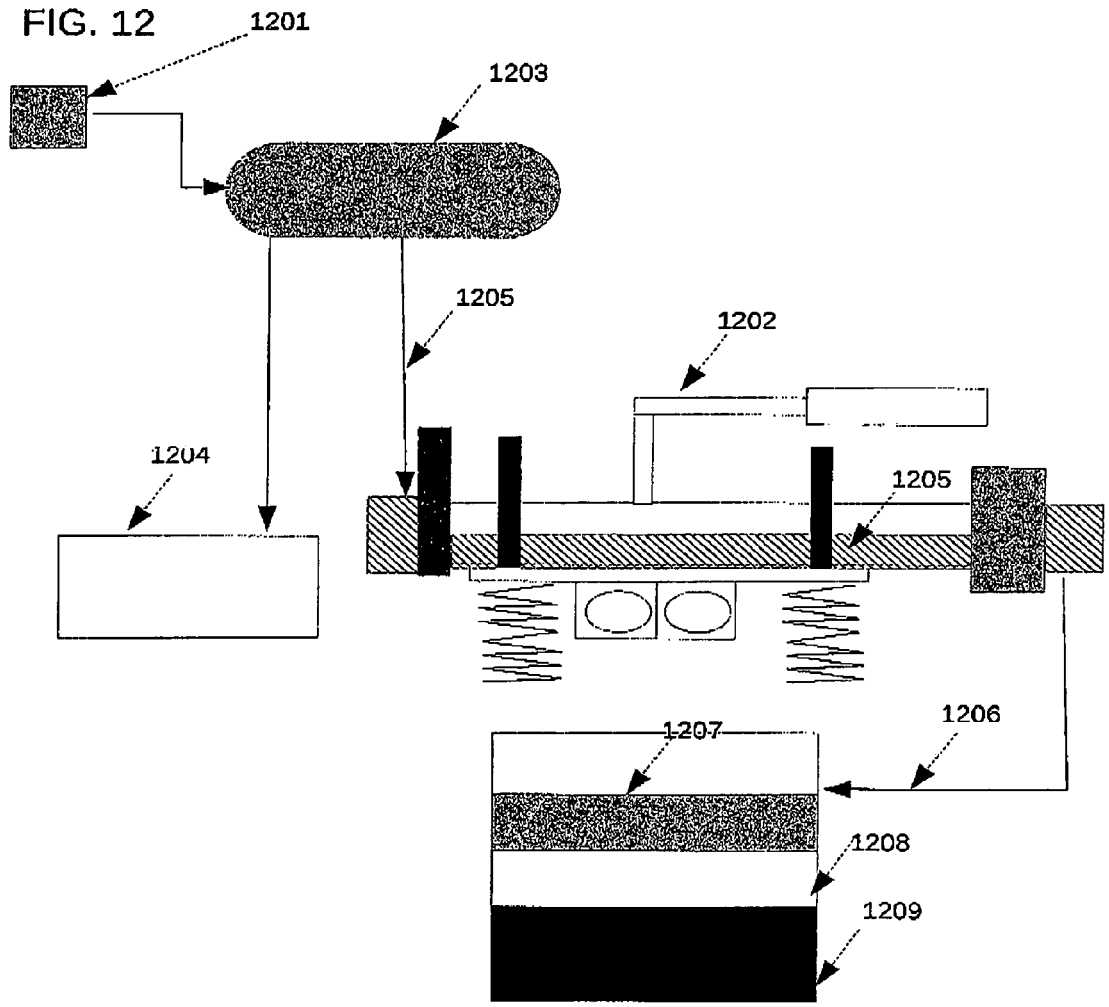
FIG. 12 shows an oil sands extraction or sands cleaning process.

FIG. 12 shows mined oil sand (1201) which is put into a crusher (1203). The crusher is connected in fluid communication to a device of FIG. 8A (1202) inside the device (1202) is a slurry from the crusher (1205). On the right end of the device (1202) the device is connected in fluid communication to a separation tank. Inside the separation tank is at the top oil (1207) in the middle water (1208) and at the bottom sand and dirt (1209).

Operation FIGS. 1A to 1D

The FIGS. 1A to 1B show a liquid which is accelerated cyclically upwards and downwards during one complete cycle.

It explains the physical effect which is widely used in this application. In a vacuum container a liquid (102) is accelerated upwards. Because there is a vacuum (101) the upwards direction (103) of the liquid generates at the bottom of the container also a vacuum gap (104). Large cavitation bubbles are formed (5) which are collapsing as the liquid moves downwards (107) generating strong shock waves (106).

This effect can be widely used in chemical processes but it has to be created much more efficient.

Operation FIG. 2

In the device of FIG. 2 two electric magnets (201) are used for cavitation generation. If the upper magnet is turned on the other magnet is turned off and if the magnet at the bottom is turned on the upper is turned off. If an ac voltage (202) is now applied to the magnets the particles (205) and objects (204) are now alternated accelerated upwards and downwards cavitation bubbles (105) at the particles (205) and objects (204) are generated. If the vacuum pump is turned on (207) a vacuum (101) is generated in a part of the vacuum container (203) increasing greatly the effect.

Operation FIG. 3

If the vacuum pump (207) is turned on a vacuum (101) is created inside a vacuum container (203) which is partly filled with a liquid (102). The two external electric vibrators (307) are running in opposite direction generating a vertical oscillation of the sieve (301) and the objects (204). The oscillation generates also cavitation bubbles as described in Operation of FIG. 2 which are cleaning the objects (204). The main advantage by this machine is that only the parts which have to be cleaned have to oscillate not the complete liquid.

Operation FIG. 4

The two external electric vibrators (307) are running in opposite direction generating a vertical oscillation of the vacuum container (203). The vacuum pump (207) generates a vacuum (101) inside the vacuum container (203). The vacuum container (203) is partly filled with a liquid (102) and vertical oscillating of the liquid generates cavitation inside the liquid (102). The springs (401) which are connected to the cover (304) of the vacuum container (203) are isolating the objects (204) from the vertical oscillation. They don't move or move much smaller than the surrounding liquid The cavitation cleans the objects (204). The main advantages of this embodiment is than the objects are not strongly shacked and this process or this machine can also be used even without using a vacuum pump (207) but the effect is not so intensive as with using the vacuum pump (207).

Operation FIG. 5

The vacuum pump (207) creates inside a vacuum container (20S) a vacuum. The vacuum container is partly filled with a liquid (102). The two electric vibrators (502) are running in opposite direction causing a vertical oscillation of the plates with holes (501). This generates also cavitation. The main advantage of this device is that the cavitation is generated directly inside the liquid.

Operation FIG. 6A

One of the most practical problems by using the in FIG. 1 described physical effect in laboratory use is; That you have to build your own adapter or containers to use the effect effectively. The embodiment described in the FIGS. 6A to 6E solve that problem.

A container with standardized connections (607) is put in rubber bumper with side restraints (610). This is done that the container (606) is not able to break out laterally if the vibration table (602) is turned on. A cover connected with a hinge (605) press the container (606) against the mounting plate so that it doesn't fly away. Because of the fact that the containers doesn't have the same height a rack (603) is used to adjust the height of the cover. The last problem is that all containers have different connections, well most of them are standardized so adapter for standardized connections is used (604). The vacuum pump (207) is turned on. It creates a vacuum inside the container (606) and also fortifies it because of the vacuum connection (303) in the bumper (610). As the vibration table (602) is turned on cavitation is generated inside the container (606). The bumper (610) and the adapter (604) prevents through the elastic behavior the container (606) from being destroyed. If the vibration table (602) is turned on liquids inside the container can reach the vacuum pump (207) and destroy it, so a separator (601) is mounted inside the vacuum connection (303).

Operation FIG. 6B

If the lock for the cover (608) is opened the container (606) can be easily changed.

Operation FIG. 6C

Not all laboratory containers are able to sustain a vacuum under pressure even if toxic or dangerous chemicals are used the destruction of a container could lead to serious damage. The embodiment of FIG. 6C solve this problem. A container is put inside vacuum container with a cover (303). Adapters for vibration protection (59/62) are put aside and below the container. This causes that the container is not destroyed while the vibration table is turned on. A vacuum pump (601) generates inside the container (303) a vacuum. The barrier (621) of the adapter (620) causes that not only the standard container (619) is evacuated but also the complete vacuum container (303). If the vibration table (602) is turned on it generates vertical oscillations and therefore cavitation inside the standard container (619).

Operation FIG. 6D to 6E

The operation of the device in FIG. 6D is very similar than the operation of the device in FIG. 6C. The only difference is that a widely used IBC container (613) is used instead of a standard container (619). The cavitation is also generated as the vacuum pump is turned on and the vibration table.

FIG. 6E works the same way. A barrel with standardized dimensions (617) is used instead of an IBC container there.

The main advantages of these devices are that the most common barrels and IBCs are not robust enough to sustain the large pressure difference if a vacuum is generated inside them.

Operation FIGS. 7A to 7C

In FIG. 7A the vacuum pump is turned on creating a vacuum inside the vacuum container. The electric vibrators are turned on. This generates cavitation inside the liquid (102). Cavitation generation is greatly increased because of the fact that plates with holes (701) are inside the container. FIG. 7C describes in detail the process. The holes in the plates (701) are used for fluid flow that the fluid is able to oscillate vertically. Cavitation is created at the plates because the plates multiplies the effect described in FIG. 1A to 1D. In FIG. 7B the plates (702) are not mounted to the container (614). They are connected to each other and put together inside the liquid (102). If a vacuum is created inside the container and the vibration table is turned on cavitation is generated.

Operation FIG. 7D

The plates (703) divides the container (207) into three independent containers. A fluid pump (707) is turned on. If the three metering valves (704) are justified that the flow into the pump is greater than the flow from the tube with the liquid (706) into the three containers a vacuum (101) is generated inside the containers. This is the fact because the left outputs are higher than the right inputs. If the two electric vibrators (502) are turned on and running in opposite directions cavitation is generated inside the containers.

In one sentence this embodiment describes how to build more vibration table based cavitation machines with only one vibration table.

Operation FIG. 8A to 8C

Because of the fact that the amount of cavitation generated increase as the bottom surface area increases. It is easily to understand that the use of a pipe can bring significant advantages. The vacuum pump is turned on generates a vacuum (101) inside the pipe (805). The separator protects the vacuum pump from being destroyed by the liquid. The fluid pump (101) pumps the liquid to the right and the metering valve (704) controls the inflow so that the correct height of the liquid inside the vacuum pipe (805) is secured. 8B is similar as 8A but the vacuum system (801) is removed. The operation is same but the height of the liquid is regulated here by the pump power and the metering valve. The fluid pump here creates the vacuum (101).

In FIG. 8C a flowing liquid in a vacuum pipe (805) is shown. The fact that the valve input and output are at different heights cause the generation of a vacuum above the upper valve input (103). The height in this example is regulated by the different heights of the vale input and outputs. In all three above mentioned examples the electric vibrators are running in opposite direction creating vertical oscillations which generates cavitation.

Operation FIG. 9A.

Cavitation can greatly increase chemical output in chemical processes. It is widely known that ultrasonic cavitation increases the productivity of biodiesel processes.

The biodiesel process described in FIG. 9A is very simple. The vegetable oil (902) in a tank is mixed with methanol and a catalyst by a device of FIG. 8A. The cavitation generates a very stable emulsion. This emulsion is then stored into a reaction tank (922). There the glycerin and the biodiesel separate. The final separation is done by a centrifugal separator (905) which separates the biodiesel from the glycerin. Because of the fact the device of FIG. 8A creates a very stable emulsion with very small droplets the reaction temperature can be reduced from 50° Celsius to 20° without any loss in chemical reaction time and output of the process. The next advantage is that less catalyst is used because of the fact that the tiny droplets in the emulsion increase the surface area of the chemical reaction partners.

Operation FIG. 9B

The biodiesel produced by the diagram in FIG. 9A is produced by transesterification. So it lays on the hand that also other transesterification processes can increased with cavitation. FIG. 9B shows a process which produces polyester plastic by transesterification. Ethylene glycol with a catalyst (908) is pumped by a metering pump (903) to the device of FIG. 8A (904) also terephthalic acid (910) is pumped by a metering pump (903) to the device of FIG. 8A (904). The two pumps secure that all components are in the right ratio. The cavitation created by the device of FIG. 8A (904) creates a stable slurry with very tiny droplets and therefore a large surface area. The slurry is pumped into an, esterification reactor (911) where it reacts at a temperature of 150° C. The esterification reactor (911) is a device of FIG. 5 which is running and generates cavitation. There are three main flows from the esterification reactor (911) the first one are unused chemicals (912) which are pumped into a separation vessel (913) which separates the waste and water (915) and the recovered feed (916) which is pump back to the process. The second flow is methanol (901) which is generated through the process and distilled.

The third flow is the feed for the polycondensation reactor (917) which is pumped into a device of FIG. 5(918). The vacuum pumps are turned on which generates a vacuum inside the devices. The electric vibrators are generating cavitation. This increases the reactivity of the polymerization reaction in this case a polycondensation reaction. The output flow from the device of FIG. 5A (918) is polyester plastic (920). There is also an output of Ethylene glycol (921) which is generated through the chemical process and distilled.

Operation FIG. 10A to 11F

Ultrasonic cavitation is widely used in wastewater treatment. The FIGS. 11 A to 11 F show the chemical, physical effects of cavitation in wastewater treatment. A cavitation bubble (105) is formed at some organic waste (1102). The bubbles collapses and destroys the organic waste (1103). So the microorganisms can easily process the waste.

Cavitation can also be used to destroy the microorganisms itself therefore intensive cavitation is used this is shown in FIG. 11E. It is possible to destroy chemicals in water with cavitation. A large cavitation bubble collapses (1102) and splits H2O into a radical —OH molecule and a Rest X the radial —OH molecule can react with other molecules in the case of FIG. 11F Ibuprofen which is split into CO2 and a not dangerous rest y.

FIG. 10 A shows the application of the in FIG. 7D described machine in a wastewater treatment plant. It is very easy how it works. The wastewater (1001) come into an aeration tank (1003) where a stirrer (1002) mixes it with the tank water. In the aeration tank (1003) air bubbles are generated (1007) for the biological treatment. A device of FIG. 7D (1004) is running at the side of tank. The water from the below is pumped into the device of FIG. 7D through a long pipe (1006) and pumped back at the top of the tank through a smaller pipe (1005). The device of FIG. 7D (1004) is turned on and generates cavitation.

In a sludge digestion device (1009) another device of FIG. 7D (1004) is used. But there for generation of intensive cavitation to destroy the microorganisms and chemicals still in the water. The sludge created in the wastewater treatment plant is a useful energy source. Therefore the sludge is pumped into a fermentation vessel (1011) and fermented to produce methane.

It is interesting for an owner of treatment plant to apply cavitation on a sludge because of the fact that cavitation can increase fermentation output in fermentation reactions.

FIG. 10B shows a device of FIG. 7D which is connected at the side of a fermentation vessel (1011). This means that to all fermentation vessels (1011) can later a cavitation generation device of FIG. 7A be added. The sludge in the fermentation vessel (1012) is pumped through a device of FIG. 7A which generates cavitation. Because of the fact that a device of FIG. 7A uses a vacuum pump the methane (1010) which is wanted is pumped by the vacuum pump to the other methane (1010) created by the fermentation vessel.

Operation FIG. 12

The mined oil sand (1201) is put into a crusher (1203) where it is mixed with hot water. This creates a slurry (1205); This slurry is pumped into a running device of FIG. 7A (1202). This creates cavitation inside the slurry. The cavitated slurry is pumped into a separation tank where the oil (1207) the water (1208) and the sand and dirt (1209) separates.

The non-usable material by the Crusher is separated directly at the crusher (1203).

The normal oil sands extraction process pumps the slurry from the crusher without applying it to cavitation and agitating the slurry very intensive in large washing drums to separate the oil from the sand. Our experiments show that we can achieve great separation even with cold water.

Conclusion, Ramification and Scope

Accordingly the reader will see that this invention is of great value for the chemical industry.

The first process description in this application is a chemical process comprising that chemical reactions are activated, accelerated or enhanced by oscillating particles or objects vertically with electric magnets inside a liquid that cavitation is generated. This process can be done in a vacuum container which is partly filled with the liquid and a vacuum. The vacuum increases greatly the cavitation generation effect. This process can be used in a lot of chemical processes because of the effect that if generates cavitation very effectively. It is only limited that in very viscous liquids cavitation cannot be created very effectively. But even is this media this process can be used for mixing applications.

Further is a mechanical device disclosed in this application (FIG. 3) which can used for cleaning applications characterized by the fact that inside a vacuum container partly filled with a liquid is an embodiment which is able to oscillate objects inside the liquid vertically that cavitation is generated at the objects.

This device is similar to the device of FIG. 5 which generates cavitation inside a liquid through vertical oscillations of three plates with holes in a vacuum container partly filled with a liquid and a vacuum. All these above mentioned processes and devices can be summarized the following way: Cavitation is generated by objects (plates with holes, particles or sieves) inside a liquid through vertical oscillations of these objects. This physical effect can be greatly increased if the liquid is inside a vacuum container, pipe or tube which are partly filed with the liquid and a vacuum. It is very easy to see that this effect can also be used for cleaning applications and it is very easy to see, that this effect can be used is a continuous process which is shown in the flow diagram of the polyester process.

For sensitive objects the cleaning device described in U.S. Pat. No. 8,147,619 B2 is not suitable to a device is shown (FIG. 4) which uses springs for vibration isolation of the objects. It is clear that not only springs can be used for vibration isolation also dampers or buffer can be used.

FIG. 6A shows an apparatus comprising: a vacuum pump with a separator in fluid communication with a removable container; an adapter to connect the removable container to the vacuum pump connection; a height adjustable cover to fortify the removable container to a vibration table which is capable of generating vertical oscillations of the removable container.

FIG. 6C shows an apparatus which is able to generate cavitation inside a removable container which is inside a vacuum container and protected by vibration protection adapters so that the container is not destroyed. FIGS. 6D and 6E show an IBC container and a barrel inside such a device.

It is clear that this apparatus is not limited only to barrels and ICBs and containers if someone has customizable adapters for example adapters that may be made larger or smaller in the operation similar to clamps or adjustable screws nearly all types of containers can be used in such apparatus if they are built large enough.

The apparatus in FIG. 7A can easily described it is a vacuum container with plates with holes for fluid flow connected in fluid communication to a vacuum pump with separator and a vibration table which is capable of generating vertical oscillations of the container.

The main advantage is that this device increases greatly the surface area of the cavitation generation effect. FIG. 7B shows that is not necessary to mount the plates directly to the container they can also be added later. To summarize the both machines it is a cavitation generation apparatus which uses plates with holes for increasing the cavitation. This effect is not only limited to plates it is also possible to use hemispheres, quarter spheres and other objects allowing the vertical oscillation of the liquid and increasing the surface area of the physical effect described in FIG. 1.

FIG. 7C shows a device which is similar to device described in U.S. Pat. No. 8,147,619 B2 for chemical reactions. But it allows with the help of a pump system and metering vales to build more of such devices with one vibration table. This approach can be adopted for use with nearly all in this application described machines. If someone combines the in the FIGS. 8A to 8C described machines with this approach he can built maybe spiral tube on a vibration table for cavitation generation.

FIG. 8A-8C are just cavitation pipes with different technical characteristics.

FIG. 9A describes a biodiesel generation process it is very easy to see that the transesterification process which is widely in the chemical industry used is not only limited to biodiesel production.

FIG. 9B shows that the cavitation created with the effect described in FIG. 1 can used for four different technical processes.

The first on is the distillation process which is enhanced by cavitation generated through vertical oscillation of the liquid or parts of the liquid. Because of the fact that distillation is very widely used in chemical industry it is very clear that this process is not only limited to the production of plastic. It can be also used in every distillation process. Even without the use of a vacuum pump.

You can use a device of FIG. 2 to generate powerful cavitation and have effective distillation.

The second process is the process of polycondensation. This is a polymerization reaction which is the third process. And as fourth process the process of transesterification.

The FIGS. 10A to 11F show that the method comprising generating cavitation in, a liquid through vertical oscillations of the liquid can be used for fermentation, wastewater cleaning processes. It depends on the intensity of the cavitation which process is increased or done.

The described fermentation process can easily adopted to other chemical industries such as pharmaceutical industry and ethanol production or other biological processes.

Every chemical process done by microorganisms can easily be increased.

FIG. 12 shows the very simply process of oil sands extraction. It is easy to see that the pipe cavitation reactor can also be used to clean dirty sands, rocks or other things in a continuous process. Also it is very easy to see that in a lot of the pipes in the chemical plants can be used as cavitation reactors if modified.

What is claimed is:

1. A method of generating cavitation in a liquid comprising:
   (i) providing a liquid with particles in a container,
   (ii) applying alternating magnetic fields to particles to accelerate the particles in opposite directions, and
   (iii) generating cavitation in the fluid by accelerating the particles.

2. The method of claim 1, further comprising applying a vacuum to the container.

3. A method of generating cavitation in a liquid comprising:
   (i) providing a vacuum container with a liquid, wherein the vacuum container contains a vibration table disposed within the vacuum container,
   (ii) applying a vacuum to the vacuum container,
   (iii) vibrating the vibration table to produce cavitation in the liquid.

4. The method of claim 3, further comprising disposing objects on the vibration table.

5. A method of generating cavitation in a liquid comprising:
   (i) providing a vacuum container with a liquid, wherein the vacuum container contains sieve suspended by at least one spring,
   (ii) applying a vacuum to the vacuum container,
   (iii) vibrating the vacuum container to produce cavitation in the liquid.

6. The method of claim 5, further comprising disposing objects on the sieve.

7. A method of generating cavitation in a liquid comprising:
   (i) providing a vacuum container with a liquid, wherein the vacuum container contains at least one plate disposed within the liquid and connected to at least one electric vibrator,
   (ii) applying a vacuum to the vacuum container,
   (iii) vibrating the plates disposed within the liquid to produce cavitation in the liquid.

8. A method of generating cavitation in a liquid comprising:
   (i) providing a removable vacuum container with a liquid and situating the vacuum container on a vibration table,
   (ii) forming a connection between the removable vacuum container and a vacuum pump,
   (iii) applying a vacuum to the vacuum container,
   (iv) vibrating the removable vacuum container with the vibration table to generate cavitation within the liquid.

9. A method for increasing fermentation output comprising:
   (i) generating a continuous flow of biomass through a vacuum container,
   (ii) applying a vacuum to the container,
   (iii) vibrating the vacuum container to produce cavitation in the liquid,
   (iv) disrupting the cell membranes of the biomass,
   (v) transportation the disrupted cells from the vacuum container to a fermenter.

10. A method for treating wastewater comprising:
    (i) generating a continuous flow of wastewater through a vacuum container,
    (ii) applying a vacuum to the container,
    (iii) vibrating the vacuum container to produce cavitation in the liquid,
    (iv) destroying chemical bonds with cavitation inside the wastewater,
    (v) destroying microorganisms with cavitation.

11. A method for separating oil sands comprising:
    (i) generating a continuous flow of oil sands water slurry through a vacuum container,
    (ii) applying a vacuum to the container,
    (iii) vibrating the vacuum container to produce cavitation in the liquid,
    (iv) generating an oil water mixture with cavitation,
    (v) transportation the oil water mixture to a separation vessel.

* * * * *